(12) United States Patent
Campbell et al.

(10) Patent No.: US 6,869,964 B2
(45) Date of Patent: Mar. 22, 2005

(54) HETEROCYCLICSULFONAMIDE HEPATITIS C VIRUS INHIBITORS

(75) Inventors: Jeffrey Allen Campbell, Cheshire, CT (US); Andrew Charles Good, Wallingford, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/441,830

(22) Filed: May 20, 2003

(65) Prior Publication Data

US 2004/0072761 A1 Apr. 15, 2004

Related U.S. Application Data

(60) Provisional application No. 60/382,104, filed on May 20, 2002.

(51) Int. Cl.[7] .................... C07D 401/02; A61K 31/47
(52) U.S. Cl. ................................ 514/312; 546/154
(58) Field of Search ......................... 546/154; 514/312

(56) References Cited

U.S. PATENT DOCUMENTS

| | | |
|---|---|---|
| 5,633,388 A | 5/1997 | Diana et al. |
| 5,866,684 A | 2/1999 | Attwood et al. |
| 5,869,253 A | 2/1999 | Draper |
| 6,018,020 A | 1/2000 | Attwood et al. |
| 6,225,284 B1 | 5/2001 | Albert et al. |
| 6,265,380 B1 | 7/2001 | Tung et al. |
| 6,268,207 B1 | 7/2001 | Bailey |
| 6,323,180 B1 | 11/2001 | Linas-Brunet et al. |
| 6,410,531 B1 | 6/2002 | Linas-Brunet et al. |
| 6,420,380 B2 | 7/2002 | Linas-Brunet et al. |
| 6,534,523 B1 | 3/2003 | Linas-Brunet et al. |
| 2002/0111313 A1 | 8/2002 | Campbell et al. |

FOREIGN PATENT DOCUMENTS

| | | |
|---|---|---|
| WO | WO 95/33764 | 12/1995 |
| WO | WO 97/06804 | 2/1997 |
| WO | WO 97/43310 | 11/1997 |
| WO | WO 98/17679 | 4/1998 |
| WO | WO 98/22496 | 5/1998 |
| WO | WO 98/46597 | 10/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/06529 | 2/2000 |
| WO | WO 00/09543 | 2/2000 |
| WO | WO 00/09558 | 2/2000 |
| WO | WO 00/10573 | 3/2000 |
| WO | WO 00/13708 | 3/2000 |
| WO | WO 00/18231 | 4/2000 |
| WO | WO 00/59929 | 10/2000 |
| WO | 1162196 A1 | 12/2000 |
| WO | WO 01/32153 A2 | 5/2001 |
| WO | WO 01/85172 A1 | 11/2001 |
| WO | WO 02/04425 A2 | 1/2002 |
| WO | WO 02/06246 A1 | 1/2002 |
| WO | WO 02/060926 A2 | 8/2002 |
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |

OTHER PUBLICATIONS

Lauer et al. (2001) New England Journal of Medicine, vol. 345, No. 1, pp. 41–52.
Zeuzem et al. (2000) The New England Journal of Medicine, vol. 343, No. 23, pp. 1666–1672.
Poynard et al. (1998) The Lancet, vol. 352, pp. 1426–1432.
Poupart et al. (2001) The Journal of Organic Chemistry, vol. 66 No. 14, pp. 4743–4751.
Steinkuhler et al. (1998) Biochemistry, vol. 37, pp. 8899–8905.
Ingallinella et al. (1998) Biochemistry, vol. 37, pp. 8906–8914.
Chu et al. (1996) Tetrahedron Letters, vol. 37 No. 40, pp. 7229–7232.
Matsumoto et al. (1996) Antiviral Research, vol. 30 No. 1, p. A23, Abstract 19.

*Primary Examiner*—Zinnia Northington Davis
(74) *Attorney, Agent, or Firm*—Warren K. Volles

(57) ABSTRACT

The present invention relates to tripeptide compounds, compositions containing such compounds and methods for using such compounds for the treatment of hepatitis C virus (HCV) infection. In particular, the present invention provides novel tripeptide analogs, pharmaceutical compositions containing such analogs and methods for using these analogs in the treatment of HCV infection.

32 Claims, No Drawings

HETEROCYCLICSULFONAMIDE HEPATITIS C VIRUS INHIBITORS

CROSS REFERENCE TO RELATED APPLICATION

The non-provisional application claims priority from the provisional application U.S. Ser. No. 60/382,104 filed May 20, 2002.

FIELD OF THE INVENTION

The present invention is generally directed to antiviral compounds, and more specifically directed to compounds which inhibit the functioning of the NS3 protease encoded by Hepatitis C virus (HCV), compositions comprising such compounds and methods for inhibiting the functioning of the NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. *N. Engl. J. Med.* (2001), 345, 41–52).

Presently, the most effective HCV therapy employs a combination of alpha-interferon and ribavirin, leading to sustained efficacy in 40% of patients. (Poynard, T. et al. *Lancet* (1998), 352, 1426–1432). Recent clinical results demonstrate that pegylated alpha-interferon is superior to unmodified alpha-interferon as monotherapy (Zeuzem, S. et al. *N. Engl. J. Med.* (2000), 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one, as yet poorly characterized, cleaves at the NS2–NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A–NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the peptide compounds disclosed in U.S. Pat. No. 6,323,180.

SUMMARY OF THE INVENTION

The present invention provides compounds, including pharmaceutically acceptable salts, solvates or prodrugs thereof, having the structure of Formula I

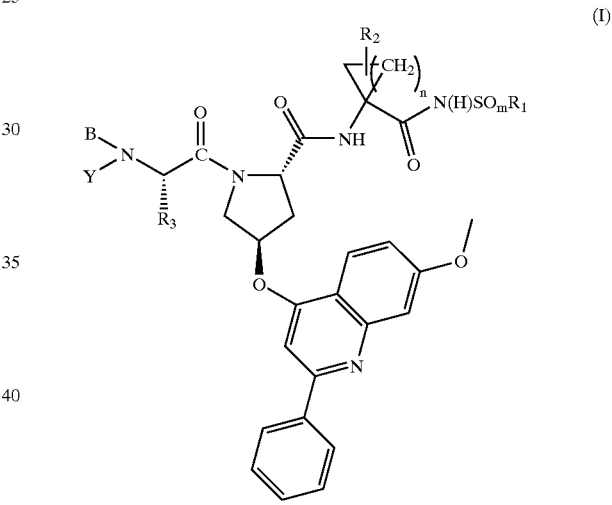

(I)

wherein:
(a) $R_1$ is unsubstituted or substituted Het, said Het substituents being the same or different and being selected from one to three of halo, cyano, trifluoromethyl, nitro, $C_{1-6}$ alkyl, $C_{1-6}$ alkoxy, amido, $C_{1-6}$ alkanoylamino, amino, phenyl or phenylthio, said phenyl or phenyl portion of phenylthio being unsubstituted or substituted by one to three, same or different, substituents selected from halo, cyano, nitro, $C_{1-6}$ alkyl, $C_{1-6}$ alkoxy, amido or phenyl;
(b) m is 1 or 2;
(a) n is 1 or 2;
(b) $R_2$ is $C_{1-6}$ alkyl, $C_{2-6}$ alkenyl or $C_{3-7}$ cycloalkyl, each optionally substituted from one to three times with halogen; or $R_2$ is H; or $R_2$ together with the carbon to which it is attached forms a 3, 4 or 5 membered ring;
(c) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(d) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;

(e) B is H, $C_{1-6}$ alkyl, $R_4$—(C=O)—, $R_4$O(C=O)—, $R_4$—N($R_5$)—C(=O)—, $R_4$—N($R_5$)—C(=S)—, $R_4$SO$_2$—, or $R_4$—N($R_5$)—SO$_2$—;

(f) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalkyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo(1.1.1)pentane; or (vi) —C(O)O$C_{1-6}$ alkyl, $C_{2-6}$alkenyl or $C_{2-6}$ alkynyl; and (i) $R_5$ is H; $C_{1-6}$ alkyl optionally substituted with 1–3 halogens; or $C_{1-6}$ alkoxy provided $R_4$ is $C_{1-10}$ alkyl;

or a pharmaceutically acceptable salt, solvate or prodrug thereof.

The present invention also provides compositions comprising the compounds or pharmaceutically acceptable salts, solvates or prodrugs thereof and a pharmaceutically acceptable carrier. In particular, the present invention provides pharmaceutical compositions useful for inhibiting HCV NS3 comprising a therapeutically effective amount of a compound of the present invention, or a pharmaceutically acceptable salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable salt, solvate or prodrug thereof. Additionally, the present invention provides methods of inhibiting HCV NS3 protease by administering to a patient an effective amount of a compound of the present invention.

By virute of the present invention, it is now possible to provide improved drugs comprising the compounds of the invention which can be effective in the treatment of patients infected with HCV. Specifically, the present invention provides peptide compounds that can inhibit the functioning of the NS3 protease, e.g., in combination with the NS4A protease.

DETAILED DESCRIPTION OF THE INVENTION

Stereochermical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine, include all possible stable configurations, unless otherwise specifically stated. Certain radicals and combinations are defined below for purposes of illustration.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqlieous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of Formula I, and pharmaceutically acceptable salts, and solvates, e.g. hydrates. Similarly, reference to intermediates, is meant to embrace their salts, and solvates, where the context so permits. References to the compound of the invention also include the preferred compounds, e.g., compounds of Formula II–VI.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.g., organic radical, to which the subsitutent is bonded, e.g., mono-, di-, tri- or tetra-substituted, unless otherwise specifically stated.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "haloalkoxy" as used herein means the radical —O(haloalkyl) wherein haloalkyl is as defined above.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralalkyl" mean an aryl group substituted with one or more alkyl groups. Thus, a $C_{7-14}$ alkylaryl group many have from 1–8 carbon atoms in the alkyl group for a monocyclic aromatic and from 1–4 carbon atoms in the alkyl group for a fused aromatic. The aryl radicals include those substituted with typical substituents known to those skilled in the art, e.g., halo, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl (alkoxy)amine. Examples of alkylaryl groups include benzyl, butylphenyl and 1-naphthylmethyl. The terms "alkylaryloxy" and "alkylarylester" mean alkylaryl groups containing an oxygen atom and ester group, respectively.

The term "carboxyalkyl" as used herein means a carboxyl group (COOH) linked through an alkyl group as defined above and includes, for example, butyric acid.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "amino aralkyl" as used herein means an amino group substituted with an aralkyl group, such as the following amino aralkyl

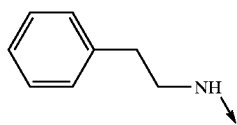

The term "alkylamide" as used herein means an amide mono-substituted with an alkyl, such as

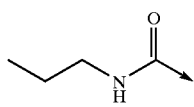

The term "carboxyalkyl" as used herein means a carboxyl group (COOH) linked through a alkyl group as defined above and includes, for example, butyric acid.

The term "heterocycle", also refered to herein or "Het", as used herein means a monovalent radical derived by removal of a hydrogen from a five-, six-, or seven-membered saturated or unsaturated (including aromatic) heterocycle containing from one to four heteroatoms selected from nitrogen, oxygen and sulfur. Further, the term heterocycle includes heterocycles as defined above that are fused to one or more other ring structures. For heterocycles containing nitrogen, the nitrogen may be substituted by $C_{1-6}$ alkyl, particularly methyl. For heterocycles containing sulfur, the oxidized sulfur heterocycles containing SO or $SO_2$ are also intended to be included. The heterocycles of the present invention include those substituted with typical substituents known to those skilled in the art on any of the ring carbon atoms, e.g., one to three substituents. Examples of such substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, ,amino, $C_{1-6}$alkylamino, di($C_{1-6}$)alkylamino, di($C_{1-6}$) alkylamide, carboxyl, ($C_{1-6}$)carboxyester, $C_{1-6}$ alkylsulfone, $C_{1-6}$ alkylsulfonamide, $C_{1-6}$ alkylsulfoxide, di($C_{1-6}$)alkyl (alkoxy)amine, $C_{6-10}$ aryl, $C_{7-14}$ alkylaryl, and a 5–7 membered monocyclic heterocycle. Examples of suitable heterocycles include, but are not limited to,

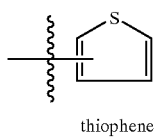
thiophene

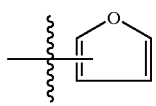
furan

-continued

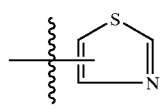
thiazole

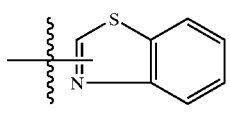
benzothiazole

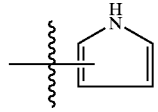
pyrrole

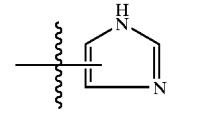
imidazole

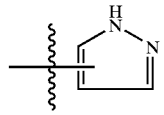
pyrazole

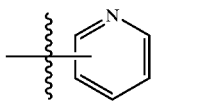
pyridine

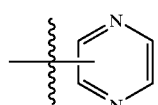
pyrazine

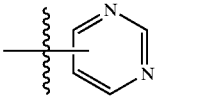
pyrimidine

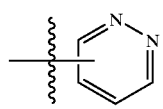
pyridazine

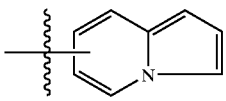
indolizine

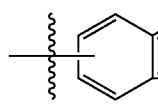
isoindole

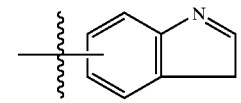
3H-indole

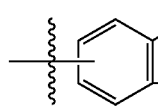
indole

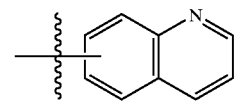
quinoline

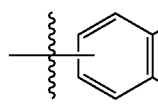
isoquinoline

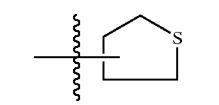
tetrahydrothiophene

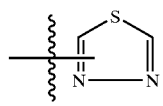
thiadiazole

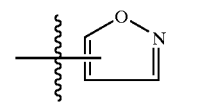
isoxazole

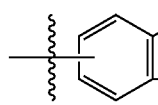
benzothiophene

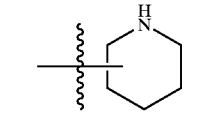
piperidine

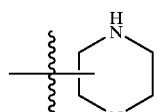
piperazine

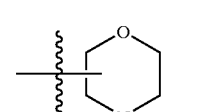
morpholine or

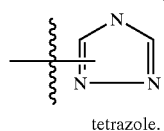

tetrazole.

The term "alkyl-heterocycle" as used herein, means a heterocyclic radical as defined above linked through a chain or branched alkyl group, wherein alkyl as defined above containing the indicated number carbon atoms. Examples of $C_{1-6}$ alkyl-Het include:

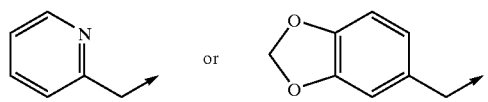

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.)(see Berger A. & Schechter I., Transactions of the Royal Society London series (1970), B257, 249–264].

Thus in the compounds of formula I, the "P1' to P4" portions of the molecule are indicated below:

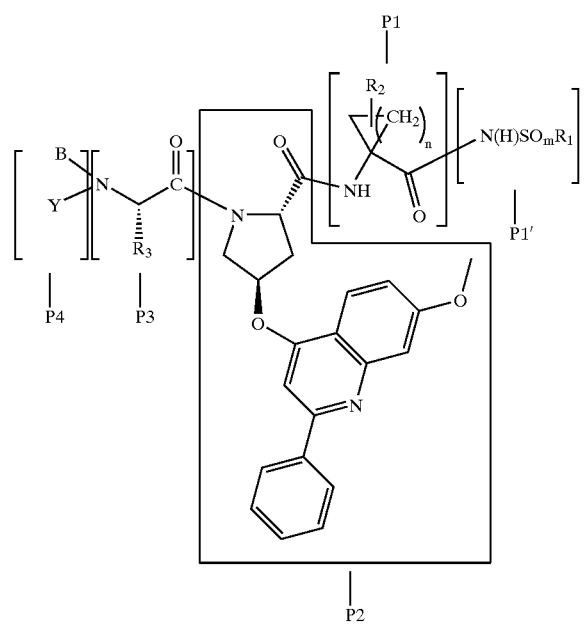

As used herein the term "1-aminocyclopropyl-carboxylic acid" (Acca) refers to a compound of formula:

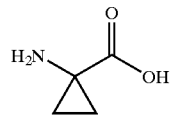

As used herein the term "tert-butylglycine" refers to a compound of the formula:

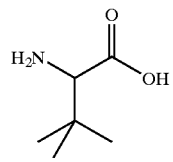

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

For compounds of the present invention, it is preferred that m is 2. It is also preferred that n is 1. It is additionally preferred that $R_2$ is ethyl or ethenyl.

In accordance with the present invention, $R_1$ may be unsubstituted or substituted Het, said Het substituents being the same or different and being selected from one to three of halo, cyano, trifluoromethyl, nitro, $C_{1-6}$ alkyl, $C_{1-6}$ alkoxy, amido, $C_{1-6}$ alkanoylamino, amino, phenyl or phenylthio, said phenyl or phenyl portion of phenylthio being unsubstituted or substituted by one to three, same or different, substituents selected from halo, cyano, nitro, $C_{1-6}$ alkyl, $C_{1-6}$ alkoxy, amido or phenyl. Preferably, $R_1$ is

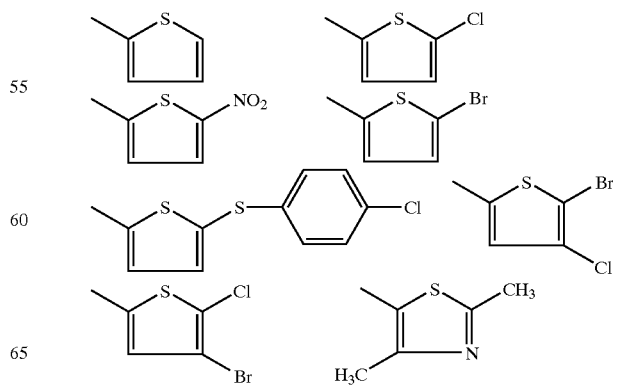

-continued

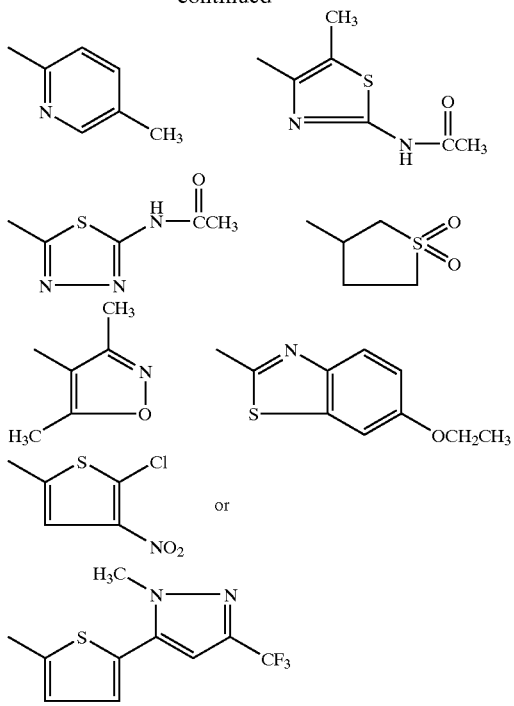

In accordance with the present invention, $R_2$ may be $C_{1-6}$ alkyl, $C_{2-6}$ alkenyl or $C_{3-7}$ cycloalkyl, each optionally substituted from one to three times with halogen; or $R_2$ is H; or $R_2$ together with the carbon to which it is attached forms a 3, 4 or 5 membered ring. Preferably, $R_2$ is $C_{1-6}$ alkyl, $C_{2-6}$ alkenyl or $C_{3-7}$ cycloalkyl. More preferably, $R_2$ is ethyl or vinyl.

In accordance with the present invention, $R_3$ may be $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl. Preferably, $R_3$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl. More preferably, $R_3$ is $C_{1-8}$ alkyl optionally substituted with $C_{1-6}$ alkoxy; or $C_{3-7}$ cycloalkyl, e.g., $C_{1-6}$ alkyl. Most preferably, $R_3$ is t-butyl.

In accordance with the present invention, Y may be H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;

In accordance with the present invention, B may be H, $C_{1-6}$ alkyl, $R_4$—(C=O)—, $R_4$O(C=O)—, $R_4$—N($R_5$)—C(=O)—, $R_4$—N($R_5$)—C(=S)—, $R_4$SO$_2$—, or $R_4$—N($R_5$)—SO$_2$—. Preferably, B is $R_4$—(C=O)—, $R_4$O(C=O)—, or $R_4$—N($R_5$)—C(=O)—.

In accordance with the present invention, $R_4$ may be (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo(1.1.1) pentane; or (vi) —C(O)O$C_{1-6}$ alkyl, $C_{2-6}$alkenyl or $C_{2-6}$ alkynyl. Preferably, $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen. More preferably, $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl. Most preferably, $R_4$ is t-butyl.

In accordance with the present invention, $R_5$ may be H; $C_{1-6}$ alkyl optionally substituted with 1–3 halogens; or $C_{1-6}$ alkoxy provided $R_4$ is $C_{1-10}$ alkyl. Preferably, $R_5$ is H or $C_{1-6}$ alkyl optionally substituted with 1–3 halogens. More preferably, $R_5$ is H.

The substituents from each grouping may be selected individually and combined in any combination which provides a stable compound in accordance with the present invention. Also, more than one substituent from each group may be substituted on the core group provided there are sufficient available binding sites.

In a preferred embodiment, compounds of the present invention have the structure of Formula II Formula II

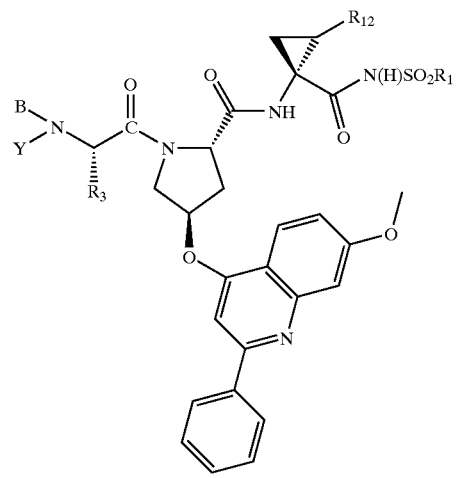

wherein $R_3$, $R_1$, B and Y are as defined in Formula I while $R_{12}$ is $C_{1-6}$ alkyl, $C_{2-6}$ alkenyl or H.

The present invention further comprises salts and solvates of compounds of Formula II, as well as pharmaceutical compositions comprising compounds of Formula II, or salts or solvates thereof.

In another preferred embodiment, compounds of the present invention have the structure of Formula III Formula III

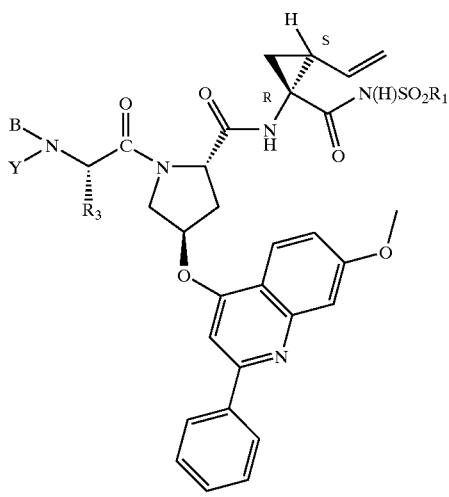

wherein $R_3$, $R_1$, B and Y are as defined in Formula I. The present invention further comprises salts or solvates of compounds of Formula III, as well as pharmaceutical compositions comprising compounds of Formula III, or salts or solvates thereof.

In another preferred embodiment, compounds of the present invention have the structure of Formula IV Formula IV

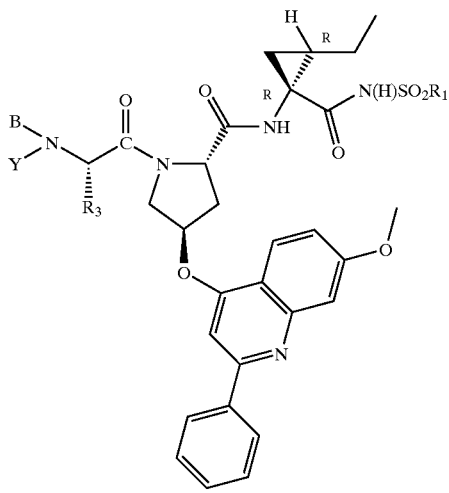

wherein $R_3$, $R_1$, B and Y are as defined in Formula I. The present invention further comprises salts or solvates of compounds of Formula IV, as well as pharmaceutical compositions comprising compounds of Formula IV, or salts or solvates thereof.

Another preferred embodiment are the compounds of Formula V

Formula V wherein $R_3$, $R_1$, n, B and Y are as defined in Formula I, and p is 1–5.

The compounds of the present invention include diastereomers of the spiral functionality of the compounds of Formula V wherein the diastereomers are either in a mixture or are a single diastereomer which has been individually prepared or has been isolated from a diastereomeric mixture.

The present invention further comprises salts and solvates of compounds of Formula V, as well as pharmaceutical compositions comprising compounds of Formula V, or salts or solvates thereof.

In yet another alternate preferred embodiment, compounds of the present invention have the following structural formula Formula VI wherein:
(a) $R_1$ is unsubstituted or substituted Het, said Het substituents being the same or different and being selected from one to three of halo, cyano, trifluoromethyl, nitro, $C_{1-6}$ alkyl, $C_{1-6}$ alkoxy, amido, $C_{1-6}$ alkanoylamino, amino, phenyl or phenylthio, said phenyl or phenyl portion of phenylthio being unsubstituted or substituted by one to three, same or different, substituents selected from halo, cyano, nitro, $C_{1-6}$ alkyl, $C_{1-6}$ alkoxy, amido or phenyl;

(b) n is 1 or 2;

(c) $R_{32}$ is H, $C_{1-6}$ alkyl, $C_{1-3}$ alkoxy, $C_{3-7}$ cycloalkyl, $C_{2-6}$ alkenyl, or $C_{2-6}$ alkynyl, all optionally substituted with halogen;

(d) $R_{33}$ is $C_{1-8}$ alkyl, $C_{3-12}$ alkenyl, $C_3$–$C_7$ cycloalkyl, $C_{4-13}$ cycloalkenyl, or $C_4$–$C_{10}$ (alkylcycloalkyl), all optionally substituted with hydroxy, $C_{1-6}$ alkoxy, $C_1$–$C_6$ thioalkyl, amino, amido, (loweralkyl) amido, $C_6$ or $C_{10}$ aryl, or $C_7$–$C_{1-6}$ aralkyl;

(e) $Y_2$ is H or $C_1$–$C_6$ alkyl;

(f) $B_2$ is H, $R_{14}$—(C=O)—; $R_{14}O(C=O)$—, $R_{14}$—N($R_{15}$)—C(=O)—; $R_{14}$—N($R_{15}$)—C(=S)—; $R_{14}SO_2$—, or $R_{14}$—N($R_{15}$)—SO_2—;

(g) $R_{14}$ is (i) $C_{1-10}$ alkyl optionally substituted with carboxyl, $C_{1-6}$ alkanoyl, hydroxy, $C_{1-6}$ alkoxy, amino optionally mono-or-di substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, all optionally substituted with hydroxy, carboxyl, ($C_{1-6}$ alkoxy) carbonyl, amino optionally monosubstituted or disubstituted with $C_{1-6}$ alkyl, amido, or (lower alkyl) amido; (iii) amino optionally monosubstituted or disubstituted with $C_{1-6}$ alkyl; amido; or (lower alkyl)amido; (iv) $C_6$ or $C_{10}$ aryl or $C_{7-16}$ aralkyl, all optionally substituted with $C_{1-6}$ alkyl, hydroxy, amido, (lower alkyl) amido, or amino optionally monosubstituted or disubstituted with $C_{1-6}$ alkyl; or (v) Het or (lower alkyl)-Het, both optionally substituted with $C_{1-6}$alkyl, hydroxy, amido, (lower alkyl) amido, or amino optionally monosubstituted or disubstituted with $C_{1-6}$ alkyl; and (h) $R_{15}$ is H or $C_{1-6}$ alkyl.

A more preferred group of compounds of the present invention are those having the formula

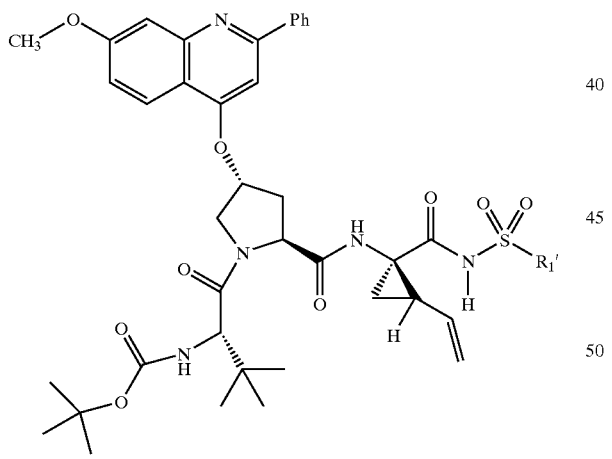

wherein $R_1'$ is

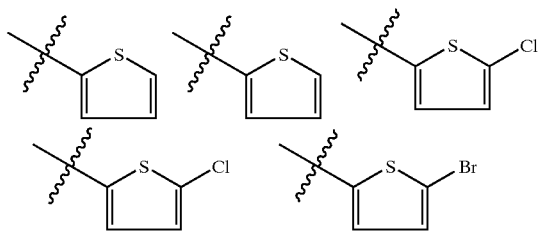

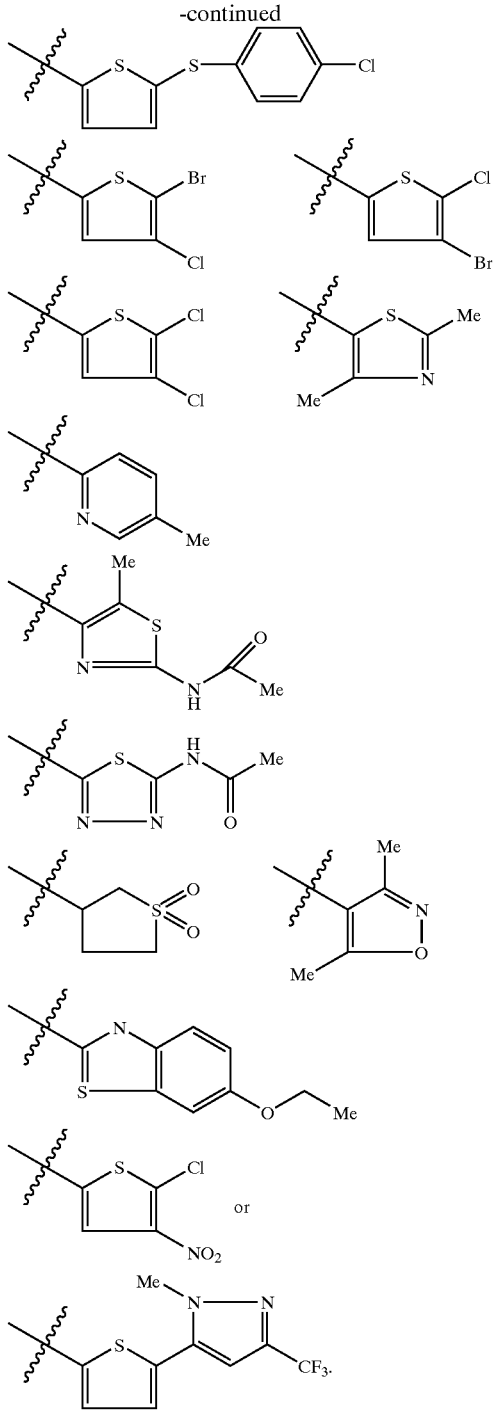

The present invention further comprises salts and solvates of compounds of Formula VI, as well as pharmaceutical compositions comprising compounds of Formula VI, or salts or solvates thereof.

The compounds of the present invention, when in a basic form, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylaamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The compounds of the present invention also contain two or more chiral centers. For example, the compounds may include P1 cyclopropyl element of formula

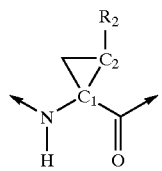

P1 wherein $C_1$ and $C_2$ each represent an asymmetric carbon atom at positions 1 and 2 of the cyclopropyl ring. Notwithstanding other possible asymmetric centers at other segments of the compounds, the presence of these two asymmetric centers means that the compounds can exist as racemic mixtures of diastereomers, such as the diastereomers wherein $R_2$ is configured either syn to the amide or syn to the carbonyl as shown below.

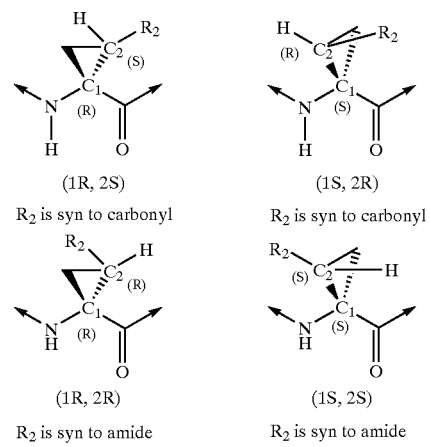

The present invention includes both enantiomers and mixtures of enantiomers such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy) alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art, see e.p., U.S. Pat. No. 6,323,180 and U.S. patent application Ser. No. 20020111313 A1. The following methods set forth below are provided for illustrative purposes and are not intended to limit the scope of the claimed invention. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

The compounds of the present invention may, for example, be synthesized according to a general process as illustrated in Scheme I (wherein CPG is a carboxyl protecting group and APG is an amino protecting group):

Scheme I

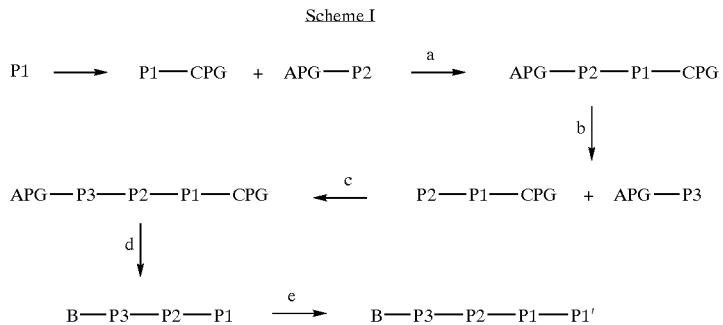

Briefly, the P1, P2, and P3 can be linked by well known peptide coupling techniques. The P1, P2, and P3 groups may be linked together in any order as long as the final compound corresponds to peptides of the invention. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodlimide (dicyclohexylcarbodiimide, diisopropylcarbodiimide, or water-soluble carboduimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N, N, N', N'-tetramethyluronium tetrafluoroborate. Still another practical and useful coupling agent is commercially available O-(7-azabenzotrizol-1-yl)-N,N,N',N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6)trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available. The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; bencyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

Further, the following guidance may be followed in the preparation of compounds of the present invention. For example, to form a compound where $R_4$—C(O)—, $R_4$—S(O)$_2$, a protected P3 or the whole peptide or a peptide segment is coupled to an appropriate acyl chloride or sulfonyl chloride respectively, that is either commercially available or for which the synthesis is well known in the art. In preparing a compound where $R_4O$—C(O)—, a protected P3 or the whole peptide or a peptide segment is coupled to an appropriate chloroformate that is either commercially available or for which the synthesis is well known in the art. For Boc-derivatives (Boc)$_2$O is used.

For example:

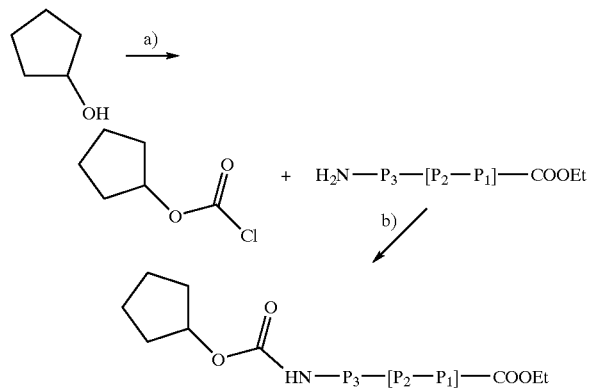

Cyclopentanol is treated with phosgene to furnish the corresponding chloroformate.

The chloroformate is treated with the desired NH$_2$-tripeptide in the presence of a base such as triethylamine to afford the cyclopentylcarbamate.

In preparing a compound where $R_4$—N(R$_5$)—C(O)—, or $R_4$—NH—C(S)—, a protected P3 or the whole peptide or a peptide segment is treated with phosgene followed by amine as described in SynLett. February 1995; (2); 142–144 or is reacted with the commercially available isocyanate and a suitable base such as triethylamine.

In preparing a compound where $R_4$—N(R$_5$)—S(O$_2$), a protected P3 or the whole peptide or a peptide segment is treated with either a freshly prepared or commercially available sulfamyl chloride followed by amine as described in patent Ger. Offen.(1998), 84 pp. DE 19802350 or WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R_1SO_2NH_2$ [prepared by treatment of $R_1SO_2Cl$ in ammonia saturated tetrahydrofuran solution] in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, effectively assembling the tripeptide P1'-P1-P2-P3-APG. Typically, in this process, 1–5 equivalents of P1' coupling agents are used.

Furthermore, if the P3 protecting group APG is removed and replaced with a B moiety by the methods described above, and the resulting α-carboxylic acid resulting from cleavage (resulting from cleavage by mild acid, mild base treatment or mild reductive means) is coupled with a $R_1SO_2NH_2$ [prepared by treatment of $R_1SO_2Cl$ in ammonia saturated tetrahydrofuran solution or alternative methods described herein] in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, the tripeptide P1'-P1-P2-P3-B is prepared. Typically, in this process, 1–5 equivalents of P1' coupling agents are used.

Compounds of the present invention can be prepared by many methods including those described in the examples, below, and as described in U.S. Pat. No. 6,323,180 and U.S. patent application Ser. No. 10/001,850 filed on Nov. 20, 2001. The teachings of U.S. Pat. No. 6,323,180 and U.S. patent application Ser. No. 10/001,850 are incorporated herein, in their entirety, by reference.

The present invention also provides compositions comprising a compound of the present invention, or a pharmaceutically acceptable salt, solvate or prodrug thereof, and a pharmaceutically acceptable carrier. Pharmaceutical compositions of the present invention comprise a therapeutically effective amount of a compound of the invention, or a pharmaceutically acceptable salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents and suspending agents. The details concerning the preparation of such compounds are known to those skilled in the art.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable carriers for the above noted compositions can be found in standard pharmaceutical texts, e.g. in "Remington's Pharmaceutical Sciences", 19 th ed., Mack Publishing Company, Easton, Pa., 1995. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable salts, solvates or prodrugs are formulated together with a pharmaceutically acceptable carrier, the resulting composition may be administered in vivo to mammals, such as man, to inhibit HCV NS3 protease or to treat or prevent HCV virus infection. Such treatment may also-be achieved using the compounds of this invention in combination with agents which include, but are not limited to: immunomodulatory agents, such as interferons; other antiviral agents such as ribavirin, amantadine; other inhibitors of HCV NS3 protease; inhibitors of other targets in the HCV life cycle such as helicase, polymerase, metalloprotease, or internal ribosome entry site; or combinations thereof. The additional agents may be combined with the compounds of this invention to create a single dosage form. Alternatively these additional agents may be separately administered to a mammal as part of a multiple dosage form.

Accordingly, another aspect of this invention provides methods of inhibiting HVC NS3 protease activity in patients by administering a compound of the present invention or a pharmaceutically acceptable salt or solvate thereof, wherein the substituents are as defined above.

In a preferred embodiment, these methods are useful in decreasing HCV NS3 protease activity in the patient. If the pharmaceutical composition comprises only a compound of this invention as the active component, such methods may additionally comprise the step of administering to said patient an agent selected from an immunomodulatory agent, an antiviral agent, a HCV protease inhibitor, or an inhibitor of other targets in the HCV life cycle such as, for example, helicase, polymerase, or metalloprotease. Such additional agent may be administered to the patient prior to, concurrently with, or following the administration of the compounds of this invention.

In an alternate preferred aspect, these methods are useful for inhibiting viral replication in a patient. Such methods can be useful in treating or preventing HCV disease.

The compounds of the invention may also be used as laboratory reagents. Compounds may be instrumental in providing research tools for designing of viral replication assays, validation of animal assay systems and structural biology studies to further enhance knowledge of the HCV disease mechanisms.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+).

Unless otherwise noted, each compound was analyzed, by LC-MS, using one of seven methodologies, having the following conditions. Note, for certain compounds, the term LC-MS is truncated to LC as MS calibaration is limited to compounds of MW 900 or less.

Columns: (Method A)—YMC ODS S7 C18 3.0×50 mm
(Method B)—YMC ODS-A S7 C18 3.0×50 mm
(Method C)—YMC S7 C18 3.0×50 mm
(Method D)—YMC Xterra ODS S7 3.0×50 mm
(Method E)—YMC Xterra ODS S7 3.0×50 mm
(Method F)—YMC ODS-A S7 C18 3.0×50 mm
(Method G)—YMC C18 S5 4.6×50 mm]
Gradient: 100% Solvent A/0% Solvent B to 0% Solvent A/100% Solvent B
Gradient time: 2 min. (A, B, D, F, G); 8 min. (C, E)
Hold time: 1 min. (A, B, D, F, G); 2 min. (C, E)
Flow rate: 5 mL/min
Detector Wavelength: 220 nm
Solvent A: 10% MeOH /90% $H_2O$/0.1% TFA
Solvent B: 10% $H_2O$/90% MeOH/0.1% TFA.

The compounds and chemical intermediates of the present invention, described in the following examples, were prepared according to the following methods.

The abbreviations used in the present application, including particularly in the illustrative examples which follow, are well-known to those skilled in the art. Some of the abbreviations used are as follows:

| | |
|---|---|
| rt | room temperature |
| Boc | tert-butyloxycarbonyl |
| DMSO | dimethylsulfoxide |
| EtOAc | ethyl acetate |
| t-BuOK | potassium t-butoxide |
| $Et_2O$ | diethyl ether |
| TBME | tert-butylmethyl ether |
| THF | tetrahydrofuran |
| CDI | carbonyldiimidazole |
| DBU | 1,8-diazabicyclo[5.4.0]undec-7-ene |
| TFA | trifluoroacetic acid |
| NMM | N-methylmorpholine |
| HATU | O-7-azabenzotriazol-1-yl |
| HBTU | O-{1H-benzotriazol-1-yl)-N,N,N',N'-tetramethyluronium hexafluorophosphate |
| HOBT | N-hydroxybenzotriazole |
| PyBrop | bromo-bis-pyrrolidine-phosphonium hexafluorophosphate |
| DMF | dimethylformamide |
| MeOH | methanol |

-continued

| | |
|---|---|
| EDTA | ethylenediaminetetraacetic acid |
| HRMS | high resolution mass spectrometry |
| DMAP | 4-dimethylaminopyridine |
| DIPEA | diisopropylethylamine |

Example 1

Preparation of Key Intermediate

Boc-(4R)-(2-phenyl-7-methoxyquinoline-4-oxo)-S-proline, shown below, was prepared as described in Steps 1a–c.

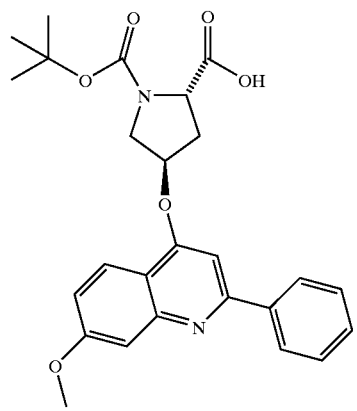

Step 1a: Preparation of 4-hydroxy-2-phenyl-7-methoxyquinoline, shown below.

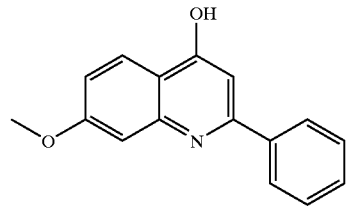

To a solution of m-anisidine (300 g, 2.44 mole) and ethyl benzoylacetate (234.2 g, 1.22 mole) in toluene (2.0 L) was added HCl (4.0 N in dioxane, 12.2 mL, 48.8 mmole). The resulting solution was refluxed for 6.5 hr using a Dean-Stark apparatus (about 56 ml of aqueous solution was collected). The mixture was cooled to rt, partitioned multiple times with aqueous HCl (10%, 3×500 mL), aqueous NaOH (1.0 N, 2×200 mL), water (3×200 mL), and the organic layer dried ($MgSO_4$) and concentrated in vacuo to supply an oily residue (329.5 g). The crude product was heated in an oil bath (280° C.) for 80 min using a Dean-Stark apparatus (about 85 mL liquid was collected). The reaction mixture was cooled down to rt, the solid residue triturated with $CH_2Cl_2$ (400 mL), the resulting suspension filtered, and the filter cake washed with more $CH_2Cl_2$ (2×150 mL).

The resulting solid was dried in vacuo (50° C.; 1 torr; 1 day) affording analytically pure 4-hydroxy-7-methoxy-2-phenylquinoline as a light brown solid (60.7 g, 20% overall). $^1$H NMR δ (DMSO): 3.86 (s, 3H), 6.26 (s, 1H), 6.94 (dd, J=9.0, 2.4 Hz, 1H), 7.21 (d, J=2.4 Hz, 1H), 7.55–7.62 (m, 3H), 7.80–7.84 (m, 2H), 8.00 (d, J=90 Hz, 1H), 11.54 (s, 1H); $^{13}$C NMR (DMSO-$d_6$) δ 55.38, 99.69, 107.07, 113.18, 119.22, 126.52, 127.17, 128.97, 130.34, 134.17, 142.27, 149.53, 161.92, 176.48. LC-MS (retention time: 1.26, method D), MS m/z 252 (M$^+$+1).

Step 1b: Preparation of 4-chloro-7-methoxy-2-phenylquinoline, shown below.

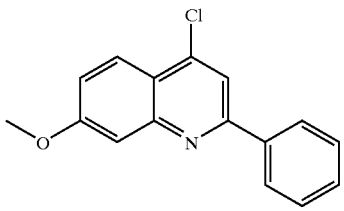

The product of Step 1a (21.7 g, 86.4 mmole) was suspended in POCl$_3$ (240 mL). The suspension was refluxed for 2 hours. After removal of the POCl$_3$ in vacuo, the residue was partitioned between EtOAc (1 L), and cold aqueous NaOH (generated from 1.0N 200 mL NaOH and 20 mL 10.0 N NaOH) and stirred for 15 min. The organic layer was washed with water (2×200 mL), brine (200 mL), dried (MgSO$_4$), and concentrated in vacuo to supply 4-chloro-2-phenyl-7-methoxyquinoline (21.0 g, 90%) as a light brown solid. $^1$H NMR (DMSO-d$_6$) δ 3.97 (s, 3H), 7.36 (dd, J=9.2, 2.6 Hz, 1H), 7.49–7.59 (m, 4H), 8.08 (d, J=9.2 Hz, 1H), 8.19 (s, 1H), 8.26–8.30 (m, 2H); $^{13}$C NMR (DMSO-d$_6$) δ: 55.72, 108.00, 116.51, 119.52, 120.48, 124.74, 127.26, 128.81, 130.00, 137.58, 141.98, 150.20, 156.65, 161.30. LC-MS (retention time: 1.547, Method D), MS m/z 270 (M$^+$+1).

Step 1c: Preparation of Boc-(4R)-(2-phenyl-7-methoxyquinoline-4-oxo)-S-proline, shown below.

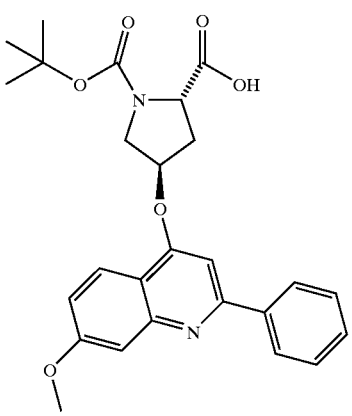

To a suspension of Boc-4R-hydroxyproline (16.44 g, 71.1 mmol) in DMSO (250 mL) was added t-BuOK (19.93 g, 177.6 mmol) at 0° C. The generated mixture was stirred for 1.5 hour and then the product of Step 1b (21.02 g, 77.9 mmol) was added in three portions over 1 h. The reaction was stirred for one day, the reaction mixture was poured into cold water (1.5 L) and washed with Et$_2$O (4×200 mL). The aqueous solution was acidified to pH 4.6, filtered to obtain a white solid, and dried in vacuo to supply the product, Boc (4R)-(2-phenyl-7-methoxyquinoline-4-oxo)proline (32.5 g, 98%). $^1$H NMR (DMSO) δ 1.32, 1.35 (two s (rotamers) 9H), 2.30–2.42 (m, 1H), 2.62–2.73 (m, 1H), 3.76 (m, 2H), 3.91 (s, 3H), 4.33–4.40 (m, 1H), 5.55 (m, 1H), 7.15 (dd, J=9.2, 2.6 Hz, 1H), 7.37 (d, J=2.6 Hz, 1H), 7.42–7.56 (m, 4H), 7.94–7.99 (m, 1H), 8.25, 8.28 (2s, 2H), 12.53 (brs, 1H); LC-MS (retention time: 1.40, Method D), MS m/z 465 (M$^+$+1).

Example 2

Preparation of Key Intermediate (1R,2S) P1 isomer of 1-{[1-2-tert-Butoxycarbonylamino-3,3-dimethylbutyryl)-4-(7-methoxy-2-phenylquinolin-4-yloxy)pyrrolidine-2-carbonyl]amino}-2-vinylcyclopropanecarboxylic acid, shown below, was prepared as described in Steps 2a–e.

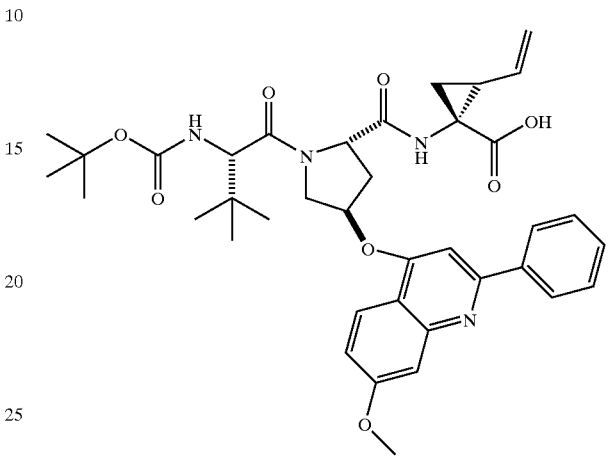

Step 2a: Preparation of (1R,2S)/(1S,2R)-1-amino-2-vinylcyclopropane carboxylic acid ethyl ester hydrochloride, shown below.

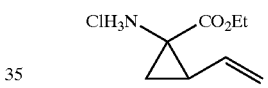

The named compound was made by each of the following methods A and B.

Method A

A.1) Preparation of N-benzyl imine of glycine ethyl ester, shown below.

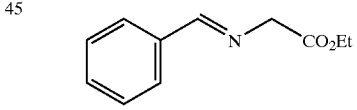

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO$_3$ (1 L) and brine (1 L). The solution was dried over MgSO$_4$, concentrated in vacuo to afford 392.4 g of the N-benzyl imine product as a thick yellow oil that was used directly in the next step. $^1$H NMR (CDCl$_3$, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

A.2) Preparation of racemic N-Boc-(1R,2S)/(1S,2R)-1-Amino-2-vinylcyclopropane carboxylic acid ethyl ester

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO$_4$) and concentrated to a volume of 1 L. To this solution of free amine, was added di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnite. The reaction mixture was dried over MgSO$_4$ and concentrated in vacuo to afford 80 g of crude material. This residue was purified by flash chromatography (2.5 Kg of SiO$_2$, eluted with 1% to 2% MeOH/CH$_2$Cl$_2$) to afford 57 g (53%) of racemnic N-Boc-(1R,2S)/(1S,2R)-1-amino-2-vinylcyclopropane carboxylic acid ethyl ester as a yellow oil which solidified while sitting in the refrigerator. $^1$H NMR (CDCl$_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd, J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M$^+$−1).

A.3) Preparation of Racemic (1R,2S)/(1S,2R) 1-Amino-2-vinylcyclopropane carboxylic acid ethyl ester hydrochloride

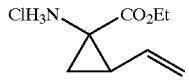

N-Boc-(1R,2S/1S,2R)-1-amino-2-vinylcyclopropane carboxylic acid ethyl ester (9.39 g, 36.8 mmol) was dissolved in 4N HCl/dioxane (90 ml, 360 mmol) and was stirred for 2 h at rt. The reaction mixture was concentrated to supply (1R,2S/1S,2R)-1-amino-2-vinylcyclopropane carboxylic acid ethyl ester hydrochloride in quantitative yield (7 g, 100%). $^1$H NMR (Methanol-d$_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2, 1H), 5.69–5.81 (m, 1H).

Method B

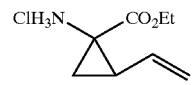

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Step 2b: Preparation of the (1R,2S) P1 isomer of 2-(1-Ethoxycarbonyl-2-vinylcyclopropylcarbamyl-4-(7-methoxyl-2-phenylquinolin-4-yloxy)pyrrollindine-1-carboxylic acid tert-butyl ester or alternative designation 2(S)-(1(R)-ethoxycarbonyl-2(S)-vinyl-cyclopropylcarbamoyl)-4(R)-(7-methoxy-2-phenyl-quinolin-4-yloxy)-pyrrolidine-1-carboxylic acid tert-butyl ester, shown below.

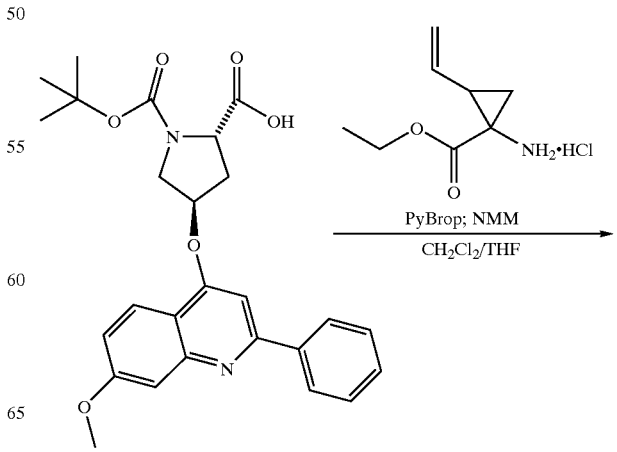

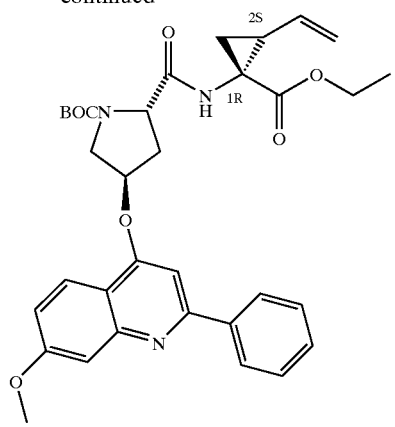

Highest Rf Isomer
and

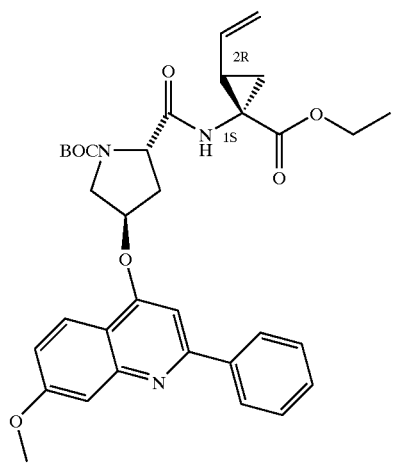

Lowest Rf Isomer

To a solution of Boc-4(R)-(2-phenyl-7-methoxyquinoline-4-oxo)proline from Step 1c (11.0 g, 23.7 mmole), HCl salt of a racemic mixture of (1R,2S) and (1S,2R) P1 derived diastereomers, from Step 2b, where carboxy group is syn to vinyl moiety (5.40 g, 28.2 mmole), NMM (20.8 mL; 18.9 mmole) in 500 mL of 50% CH$_2$Cl$_2$/THF was added the coupling reagent PyBrop or Bromotrispyrrolidino-phosphonium hexafluorophosphate (16.0 g, 34.3 mmole) in three portions in 10 min at 0° C. The solution was stirred at rt for one day and then was washed with pH 4.0 buffer (4×50 mL). The organic layer was washed with saturated aqueous NaHCO$_3$ (100 mL), the aqueous washing extracted with ethyl acetate (150 mL), and the organic layer backwashed with pH 4.0 buffer (50 mL), and saturated aqueous NaHCO$_3$ (50 mL). The organic solution was dried (MgSO$_4$), concentrated and purified using a Biotage 65M column (eluted with 50% EtOAc/Hexanes) to provide over 7.5 g of a 1:1 mixture of (1R,2S) and (1S,2R) P1 isomers of 2-(1-Ethoxycarbonyl-2-vinylcyclopropylcarbamyl-4-(7-methoxyl-2-phenylquinolin-4-yloxy)pyrrollindine-1-carboxylic acid tert-butyl ester (50% overall) or alternatively elution over a Biotage 65M column using a slow to 15% to 60% EtOAc in hexanes gradient to supply 3.54 g (25%) of the high Rf eluted (1R,2S) P1 isomer, and 3.54 g (25%) of the low Rf eluted (1S,2R) P1 isomer.

Data for (1R,2S) P1 isomer: $^1$H NMR (CDCl$_3$) δ 1.21 (t, J=7 Hz, 3H), 1.43 (s, 9H), 1.47–1.57 (m, 1H), 1.88 (m, 1H), 2.05–2.19 (m, 1H), 2.39 (m, 1H), 2.88 (m, 1H), 3.71–3.98 (m, 2H), 3.93 (s, 3H), 4.04–4.24 (m, 2H), 4.55 (m, 1H), 5.13 (d, J=10 Hz, 1H), 5.22–5.40 (m, 1H), 5.29 (d, J=17 Hz, 1H), 5.69–5.81 (m, 1H), 7.02 (brs, 1H), 7.09 (dd, J=9, 2 Hz, 1H), 7.41–7.52 (m, 4H), 7.95 (d, J=9 Hz, 1H), 8.03, 8.05 (2s, 2H); $^{13}$C NMR (CDCl$_3$) δ: 14.22; 22.83, 28.25, 33.14, 33.58, 39.92, 51.84, 55.47, 58.32, 61.30, 75.86, 81.27, 98.14, 107.42, 115.00, 117.84, 118.27, 122.63, 123.03, 127.50, 128.72, 129.26, 133.39, 140.06, 151.23, 159.16, 160.34, 161.35, 169.78, 171.68. LC-MS (retention time: 1.62, method D), MS m/z 602 (M$^+$+1).

Data for the (1S,2R) P1 isomer: $^1$H NMR δ 1.25 (t, J=7 Hz, 3H), 1.44 (s, 9H), 1.46–1.52 (m, 1H), 1.84 (m, 1H), 2.12–2.21 (m, 1H), 2.39 (m, 1H), 2.94 (m, 1H), 3.82 (m, 2H), 3.97 (s, 3H), 4.05–4.17 (m, 2H), 4.58 (m, 1H), 5.15 (d, J=10.8 Hz, 1H), 5.33 (d, J=17 Hz, 1H), 5.30–5.43 (m, 1H), 5.72–5.85 (m, 1H), 7.05 (s, 1H), 7.13 (dd, J=9, 2 Hz, 1H), 7.46–7.60 (m, 4H), 7.98 (d, J=9 Hz, 1H), 8.06–8.10 (m, 2H). LC-MS (retention time: 1.66, method D), MS m/z 602 (M$^+$+1).

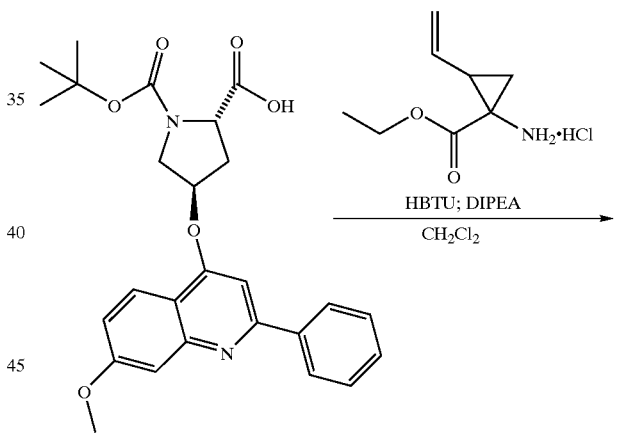

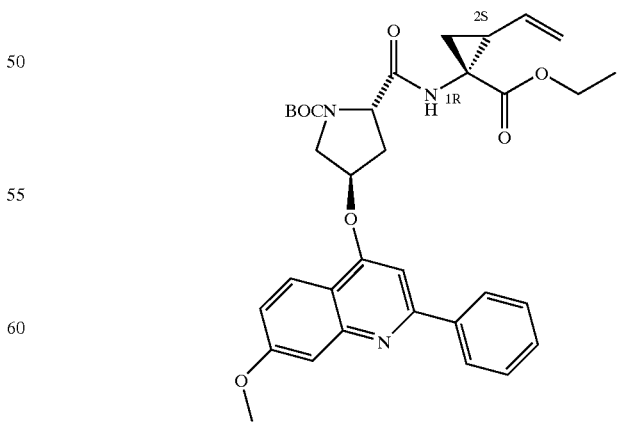

Highest Rf Isomer
and

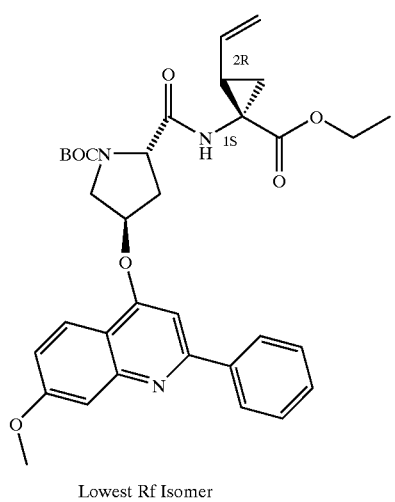

Lowest Rf Isomer

Alternative Step 2b: Preparation of 2(S)-(1(R)-ethoxycarbonyl-2(S)-vinyl-cyclopropylcarbamoyl)-4(R)-(7-methoxy-2-phenyl-quinolin-4-yloxy)-pyrrolidine-1-carboxylic acid tert-butyl ester, shown below.

The product of Step 2a (7.5 g, 39.1 mmol) was combined with diisopropylethylamine (32.5 mL, 186 mmol) in dichloromethane (150 mL). To the resulting mixture was added HOBT hydrate (6.85 g, 44.7 mmol) and the product of Step 1c (17.3 g, 37.3 mmol) followed by addition of HBTU (16.96 g, 44.7 mmol). A slight exotherm occurred immediately, and the mixture was stirred at room temperature overnight. The mixture was then concentrated in vacuo and redissolved in ethyl acetate (600 mL). The solution was washed with water (2×200 mL), then with 10% aqueous sodium bicarbonate (2×200 mL), then with water (150 mL) and finally with brine (150 mL). The organic was dried over anhydrous magnesium sulfate and filtered, and the filtrate was concentrated in vacuo to a beige glassy solid. Purification was performed in multiple batches (7 g each) by flash chromatography on a Biotage Flash 75M cartridge (66% hexanes/ethyl acetate) to provide the (1R,2S) vinyl acca P1 isomer of BOC—NH-P2-P1-COOEt as the initial eluted isomer (9.86 g total, 44.0% yield), followed by elution of the (1S,2R) vinyl acca P1 isomer of BOC—NH-P2-P1-COOEt as the second eluted isomer (10.43 g total, 46.5% yield). A total of 1.97 g of mixed fractions were recovered to give an overall conversion of 99.3% to the two diastereomers.

(1R,2S) isomer—$^1$H NMR: (methanol-d$_4$) δ 1.23 (t, J=7.2 Hz, 3H), 1.4 (s, 4H), 1.45 (s, 6H), 1.73 (dd, J=7.9, 1.5 Hz, 0.4H), 1.79 (dd, J=7.8, 2.4 Hz, 0.6H), 2.21 (q, J=8.2 Hz, 1H), 2.44–2.49 (m, 1H), 2.66–2.72 (m, 0.4H), 2.73–2.78 (m, 0.6H), 3.93–3.95 (m, 2H), 3.96 (s, 3H), 4.10–4.17 (m, 2H), 4.44 (q, J=7.8 Hz, 1H), 5.13 (d, J=10.7 Hz, 1H), 5.31 (d, J=17.7 Hz, 0.4H), 5.32 (d, J=17.4 Hz, 0.6H), 5.49 (bs, 1H), 5.66–5.82 (m, 1H), 7.16 (dd, J=9.2, 2.5 Hz, 1H), 7.26 (s, 1H), 7.42 (d, J=2.4 Hz, 1H), 7.48–7.55 (m, 3H), 8.02–8.05 (m, 3H); MS m/z 602 (M$^+$+1)

Step 2c: Preparation of the (1R,2S) P1 diastereomer of 1-{[4-(7-Methoxy-2-phenylquinolin-4yloxy)pyrrolidine-2-carbonyl]-1-amino}-2-vinylcyclopropanecarboxylic acid ethyl ester, dihydrochloride, shown below.

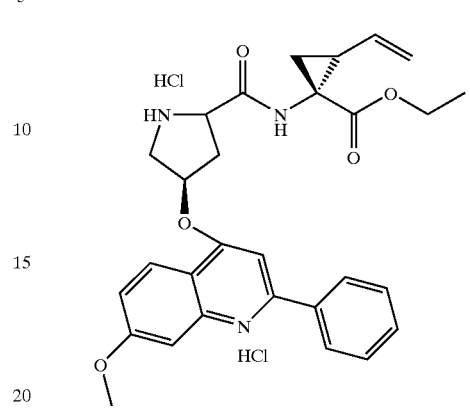

The product of Step 2b (5.88 g, 9.77 mmol) was dissolved in HCl/dioxane (4.0M; 200 ml) and was stirred for 2.5 h at rt. The reaction mixture was concentrated to supply the titled product. $^1$H NMR (Methanol-d$_4$) δ 1.24 (t, J=7 Hz, 3H), 1.50 (dd, J=10, 5 Hz, 1H), 1.78 (dd, J=8.4, 5.5 Hz, 1H), 2.24–2.33 (m, 1H), 2.56–2.66 (m, 1H), 3.05 (dd, J=14.6, 7.3 Hz, 1H), 3.98 (s, 2H), 4.06 (s, 3H), 4.15 (q, J=7 Hz, 2H), 4.76 (dd, J=10.6, 7.3 Hz, 1H), 5.13 (dd, J=10.2, 1.8 Hz), 5.32 (dd, J=17, 2 Hz), 5.70–5.83 (m, 1H), 6.05 (m, 1H), 7.48 (dd, J=9, 2 Hz, 1H), 7.65–7.79 (m, 5H), 8.12–8.15 (m, 2H), 8.54 (d, J=9.5 Hz, 1H); $^{13}$C NMR (methanol-d$_4$) δ: 14.77, 23.23, 34.86, 37.25, 41.19, 43.90, 52.66, 60.35, 62.32, 62.83, 68.27, 72.58, 73.70, 81.21, 100.70, 102.44, 116.13, 118.67, 122.25, 126.93, 130.27, 130.94, 133.19, 134.14, 134.89, 143.79, 158.39, 166.84, 167.44, 169.57, 171.33. LC-MS (retention time: 1.55, Method D), MS m/z 502 (M$^+$+1).

Step 2d: Preparation of the (1R,2S) P1 isomer of 1-{[1-2-tert-Butoxycarbonylamino-3,3-dimethyl-butyryl]-4-(7-methoxy-2-phenylquinolin-4-yloxy)p-pyrrolidine-2-carbonyl]-amino}-2-vinyl-cyclopropanecarboxylic acid ethyl ester, shown below.

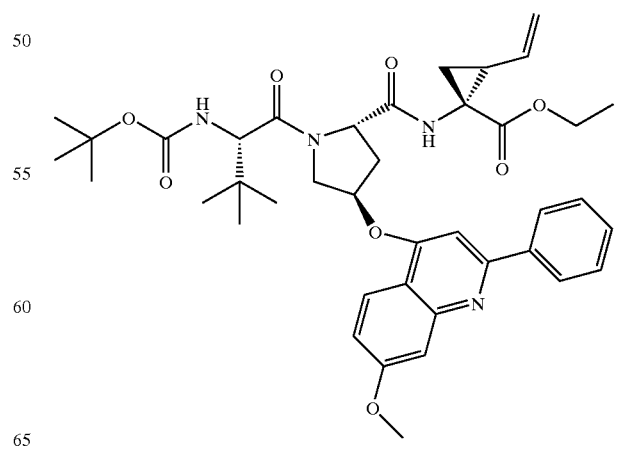

To a suspension of the product of Step 12c (1.95 g; 3.4 mmol), N-BOC-L-tert-leucine (0.94 g, 4.08 mmol), NMM (1.87 ml, 17 mmol) in DMF (15 mL) was added HATU (1.55 g, 4.08 mmol) at 0° C. After being stirred for 2 days, the reaction mixture was diluted with EtOAc (200 mL), washed with pH 4.0 buffer (2×30 mL), saturated aqueous NaHCO₃ (30 mL), brine (30 mL), dried (MgSO₄), purified by a Biotage 40 M column (eluted with 15% to 60% EtOAc in Hexanes) to supply the titled product as a white solid (2.21 g, 90%). ¹H NMR (CDCl₃) δ 1.05 (s, 9H), 1.20 (t, J=7 Hz, 3H), 1.38–1.43 (m, 1H), 1.41 (s, 9H), 1.80–1.85 (m, 1H), 2.08–2.16 (m, 1H), 2.39–2.47 (m, 1H), 2.90–2.99 (m, 1H), 3.90–4.01 (m, 1H), 3.93 (s, 3H), 4.12 (q, J=7 Hz, 2H), 4.36 (d, J=10 Hz, 1H), 4.45 (d, J=12 Hz, 1H), 4.75–4.85 (m, 1H), 5.09–5.13 (m, 1H), 5.21–5.34 (m, 2H), 5.69–5.81 (m, 1H), 7.00–7.09 (m, 2H), 7.42–7.54 (m, 5H), 8.01–8.05 (m, 3H); ¹³C NMR (CDCl₃) δ 14.30, 22.85, 26.40, 28.25, 32.20, 34.09, 35.39, 39.97, 53.86, 55.47, 58.28, 58.96, 61.29, 75.94, 79.86, 97.98, 107.43, 115.06, 117.98, 118.38, 123.03, 127.52, 128.76, 129.24, 133.40, 140.26, 151.44, 155.74, 159.16, 160.09, 161.32, 169.55, 170.64, 172.63. LC-MS (retention time: 1.85, Method D), MS m/z 715 (M⁺+1).

Step 2e: Preparation of the titled product, (1R,2S) P1 isomer of 1-{[1-2-tert-Butoxycarbonylamino-3,3-dimethylbutyryl)-4-(7-methoxy-2-phenylquinolin-4-yloxy) pyrrolidine-2-carbonyl]amino}-2-vinylcyclopropanecarboxylic acid. To a suspension of the product of Step 12d (2.63 g, 3.68 mmol) in THF(150 mL), CH₃OH (80 mL), and H₂O (20 mL) was added LiOH (1.32 g, 55.2 mmol). The reaction mixture was stirred for two days, acidified to neutral pH, and concentrated in vacuo until only the aqueous layer remained. The resulting aqueous residue was acidified to pH 3.0 by addition of 1.0 N aqueous HCl, and extracted with EtOAc (4×200 mL). Combined organic solvent was washed by brine (20 mL), dried (Na₂SO₄), filtered, and concentrated in vacuo to supply the titled product as white solid (2.41 g, 96%). ¹H NMR (CDCl₃/Methanol-d₄) δ 0.98, 1.01 (two s (rotamers) 9H), 1.40, 1.42 (two s (rotamers) 9H), 1.35–1.47 (m, 1H), 1.89–1.93 (m, 1H), 2.03–2.14 (m, 1H), 2.45–2.52 (m, 1H), 2.64–2.78 (m, 1H), 3.94 (s, 3H), 3.96–4.12 (m, 1H), 4.34 (d, J=10 Hz, 1H), 4.52 (d, J=11 Hz, 1H), 4.58–4.64 (m, 1H), 5.10 (d, J=12 Hz, 1H), 5.24 (d, J=16 Hz, 1H), 5.34 (m, 1H), 5.68–5.86 (m, 2H), 7.02–7.05 (m, 1H), 7.32 (m, 1H), 7.40–7.54 (m, 4H), 7.97–8.03 (m, 3H); ¹H NMR (Methanol-d₄) δ 1.03 (s, 9H), 1.26 (s, 9H), 1.39–1.47 (m, 1H), 1.68 (dd, J=8, 5 Hz, 1H), 2.15–2.23 (m, 1H), 2.40–2.51 (m, 1H), 2.71 (dd, J=14, 7 Hz, 1H), 3.95 (s, 3H), 4.01–4.10 (m, 1H), 4.22 (d, J=9 Hz, 1H), 4.53–4.64 (m, 1H), 5.08 (dd, J=10, 2 Hz, 1H), 5.24 (dd, J=17, 2 Hz, 1H), 5.56 (m, 1H), 5.77–5.89 (m, 1H), 7.08 (dd, J=9, 2 Hz, 1H), 7.27 (s, 1H), 7.36–7.41 (m, 1H), 7.48–7.58 (m, 3H), 8.03–8.12 (m, 3H); LC-MS (retention time: 1.64, method D), MS m/z 687 (M⁺+1).

The hydrolysis procedure disclosed in Step 2e, herein, may be used for all N-BOC tripeptides containing vinyl Acca such as the product of Step 2d.

Example 3

Compound 1, BOCNH-P3(L-t-BuGly)-P2[(4R)-(2-phenyl-7-methoxyquinoline-4-oxo)-S-proline]-P1(1R,2S Vinyl Acca)-CONH(2-sulfonylthiophene) or alternate designation, Compound 1, the (1R,2S) P1 isomer of (1-{4-(7-Methoxy-2-phenylquinolin-4-yloxy)-2-[1-(thiophene-2-sulfonylaminocarbonyl)-2-vinyl-cyclopropylcarbamoyl]-pyrrolidine-1-carbonyl}-2,2-dimethylpropyl)carbamic acid tert-butyl ester, shown below, was prepared as follows.

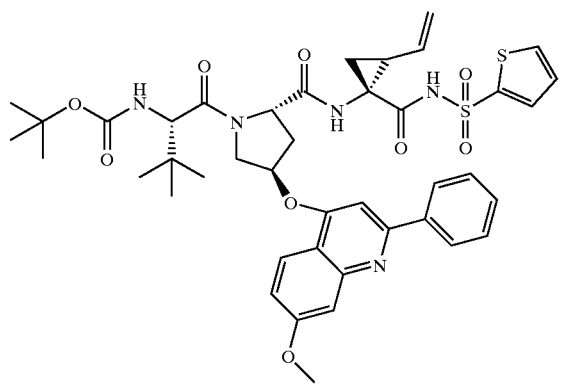

Preparation of Compound 1. Method A. A solution of CDI (0.0165 g, 0.10 mmol) and the product of Step 2e (0.050 g, 0.0728 mmol) in THF (2 mL) was refluxed for 30 min and allowed to cool down to rt. A total of 0.0594 g (0.36 mmol) of 2-thiophenesulfonamide (prepared from 2-thiophene sulfonylchloride purchased from Aldrich using the method of Steinkopf and Hoepner, *Justus Liebigs Ann. Chem.*, 501, 1933, p. 174–182), followed by the addition of a solution of neat DBU (0.025 mL, 0.167 mmol). The reaction was stirred for 18 h, diluted with EtOAc (30 mL) and washed pH 4.0 buffer (3×10 mL), dried (MgSO₄), concentrated and purified over one 1000 □M preparative TLC plate from Analtech (20×40 cm, eluted sequentially with 0% to 6% MeOH in CH₂Cl₂) to supply Compound 1 (0.0298 g, 49%): ¹H NMR (methanol-d₄, 500 MHz) □ 1.02 (s, 9H), 1.26 (s, 9H), 1.31–1.32 (m, 1H), 1.75–1.78 (m, 1H), 2.03–2.08 (m, 1H), 2.44–2.53 (m, 1H), 2.62–2.66 (m, 1H), 3.91 (s, 3H), 4.07–4.09 (m, 1H), 4.23 (s, 1H), 4.47 (d, J=12 Hz, 1H), 4.52–4.56 (m, 1H), 4.88–4.91 (m, 1H), 5.11 (d, J=17 Hz, 1H), 5.45 (m, 1H), 5.78–5.90 (m, 1H), 6.95 (m, 1H), 7.04 (d, J=9 Hz, 1H), 7.19 (s, 1H), 7.34 (s, 1H), 7.43–7.65 (m, 4H), 7.62 (s, 1H), 8.02–8.09 (m, 3H); LC-MS (retention time: 1.91, Method D), MS m/z 832 (M⁺+1).

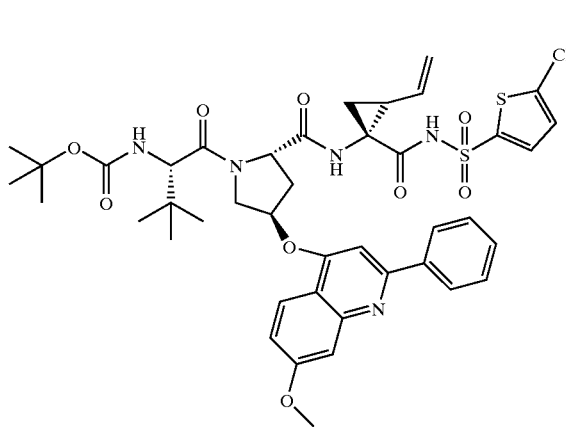

2

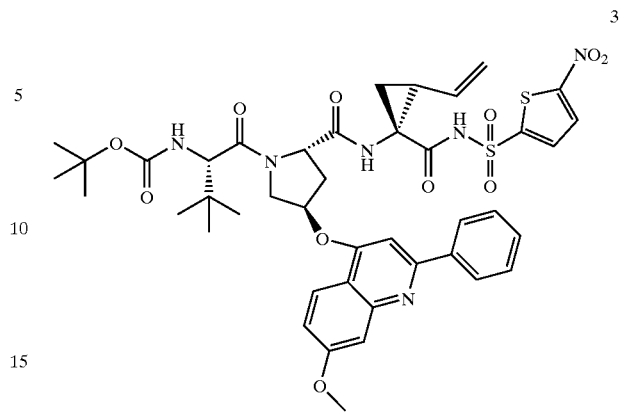

3

Example 4

Compound 2, BOCNH-P3(L-t-BuGly)-P2[(4R)-(2-phenyl-7-methoxyquinoline-4-oxo)-S-proline]-P1 (1R,2S Vinyl Acca)-CONH(2-sulfonyl-5-chlorothiophene) or alternate designation, Compound 2, the (1R,2S) P1 isomer of (1-{4-(7-Methoxy-2-phenylquinolin-4-yloxy)-2-[1-(5-Chlorothiophene-2-sulfonylaminocarbonyl)-2-vinyl-cyclopropylcarbamoyl]-pyrrolidine-1-carbonyl}-2,2-dimethylpropyl)carbamic acid tert-butyl ester, shown above, was prepared as follows.

Preparation of Compound 2. Method B. A solution of CDI (0.0165 g, 0.10 mmol) and the product of Step 2e (0.035 g, 0.050 mmol) in THF (2 mL) was refluxed for 30 min and allowed to cool down to rt. A total of 0.0403 g (0.20 mmol) of 5-chloro-2-thiophenesulfonamide (prepared from 2-thiophene sulfonylchloride purchased from Aldrich and converted to the primary sulfonamide in analogous fashion to the method of Steinkopf and Hoepner, *Justus Liebigs Ann. Chem.*, 501, 1933, p.174–182), followed by the addition of a solution of neat DBU (0.0194 mL, 0.13 mmol). The reaction was stirred for 18 h, diluted with EtOAc (100 mL) and washed with pH 4.0 buffer (3×10 mL), brine (10 mL), dried (MgSO$_4$) and concentrated. The residue was purified initially over a Isco 10 g column (eluted with 0% to 10% MeOH/CH$_2$Cl$_2$, followed by a final purification over one 1000 □M preparative TLC plate from Analtech (20×40 cM, eluted with 2.5% to 5% MeOH in CH$_2$Cl$_2$) to supply Compound 2 (0.0159 g, 37%): $^1$H NMR (methanol-d$_4$, 500 MHz) □ 1.03, 1.04 (2s, 9H total), 1.26, 1.28 (2s, 9H total), 1.33–1.46 (m, 1H), 1.76–1.79 (m, 1H), 2.11–2.16 (m, 1H), 2.40–2.50 (m, 1H), 2.69 (dd, J=14, 7 Hz, 1H), 3.96 (s, 3H), 4.04–4.14 (m, 1H), 4.19–4.24 (m, 1H), 4.53–4.58 (m, 2H), 4.97 (d, J=10 Hz, 1H), 5.17 (d, J=17 Hz, 1H), 5.60–5.66 (m, 2H), 7.00 (d, J=4 Hz, 1H), 7.13 (dd, J=9, 2 Hz, 1H), 7.32 (s, 1H), 7.40 (d, J=2 Hz, 1H), 7.53–7.58 (m, 4H), 8.04–8.05 (m, 2H), 8.13–8.17 (m, 1H); LC-MS (retention time: 1.76, Method A), MS m/z 866 (M$^+$+1).

Example 5

Compound 3, BOCNH-P3(L-t-BuGly)-P2[(4R)-(2-phenyl-7-methoxyquinoline-4-oxo)-S-proline]-P1(1R,2S Vinyl Acca)-CONH(2-sulfonyl-5-nitrothiophene) or alternate designation, Compound 3, the (1R,2S) P1 isomer of (1-{4-(7-Methoxy-2-phenylquinolin-4-yloxy)-2-[1-(5-Nitrothiophene-2-sulfonylaminocarbonyl)-2-vinyl-cyclopropylcarbamoyl]pyrrolidine-1-carbonyl}-2,2-dimethylpropyl)carbamic acid tert-butyl ester, shown above, was prepared in analogous fashion to that of compound 2 but using 5-nitrothiophene-2-sulfonamide purchased from Salor as the primary sulfonamide: LC-MS (retention time: 5.19, Method E), MS m/z 878 (M$^+$+1).

4

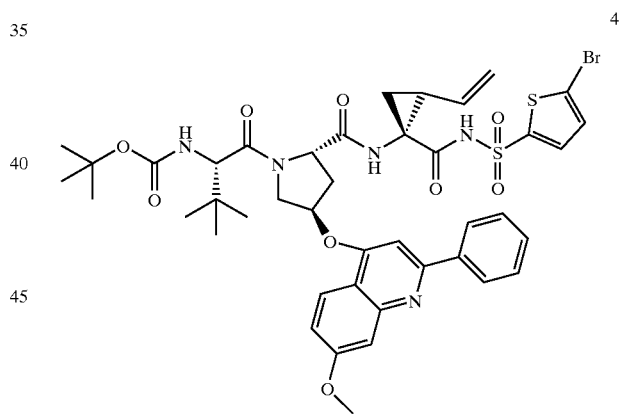

Example 6

Compound 4, BOCNH-P3(L-t-BuGly)-P2[(4R)-(2-phenyl-7-methoxyquinoline-4-oxo)-S-proline]-P1(1R,2S Vinyl Acca)-CONH(2-sulfonyl-5-bromothiophene) or alternate designation, Compound 4, the (1R,2S) P1 isomer of (1-{4-(7-Methoxy-2-phenylquinolin-4-yloxy)-2-[1-(5-Bromothiophene-2-sulfonylaminocarbonyl)-2-vinyl-cyclopropylcarbamoyl]pyrrolidine-1-carbonyl}-2,2-dimethylpropyl)carbamic acid tert-butyl ester, shown above, was prepared in analogous fashion to that of compound 2 but using 5-bromothiophene-2-sulfonamide purchased from Oakwood as the primary sulfonamide: $^1$H NMR (methanol-d$_4$, 300 MHz) □ 1.02 (s, 9H), 1.26 (s, 9H), 1.43 (m, 1H), 1.78 (dd, J=8, 5 Hz, 1H), 2.05–2.11 (m, 1H), 2.46–2.55 (m, 1H), 2.63–2.72 (m, 1H), 3.91, 3.93 (2s, 3H), 4.05–4.14 (m, 1H), 4.23 (s, 1H), 4.46–4.62 (m, 2H), 4.90–4.94 (m, 1H), 5.13 (d, J=17.2 Hz, 1H), 5.43–5.48 (m, 1H), 5.66–5.88 (m, 1H), 6.96–6.99 (m, 1H), 7.03–7.06 (m, 1H), 7.20 (s, 1H), 7.34–7.37 (m, 2H), 7.47–7.55 (m, 3H), 8.01–8.11 (m, 3H). HRMS calcd. for $C_{42}H_{49}N_5O_9S_2$: 910.2155, found 910.2164. LC (retention time: 1.75, Method A).

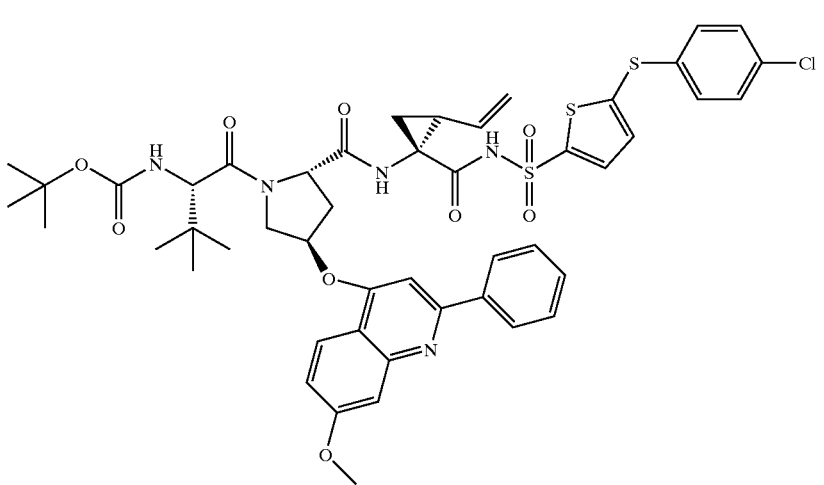

5

Example 7

Compound 5, BOCNH-P3(L-t-BuGly)-P2[(4R)-(2-phenyl-7-methoxyquinoline-4-oxo)-S-proline]-P1(1R,2S VinylAcca)-CONH(2-sulfonyl-5-[4-chlorophenylsulf-anyl]thiophene) or alternate designation, Compound 5, the (1R, 2S) P1 isomer of {1-[2-{1-[5-(4-Chlorophenylsulfanyl)-thiophene-2-sulfonylamino-carbonyl]-2-vinyl-cyclopropylcarbamoyl}-4-(7-methoxy-2-phenyl-quinolin-4-yloxy)-pyrrolidine-1-carbonyl]-2,2-dimethylpropyl}carbamic acid tert-butyl ester, shown above, was prepared in analogous fashion to that of compound 2 but using 5-bromothiophene-2-sulfonamide purchased from Maybridge as the primary sulfonamide: $^1$H NMR (methanol-d$_4$, 300 MHz) δ 1.01 (s, 9H), 1.27 (s, 9H), 1.43 (m, 1H), 1.77 (dd, J=8, 5 Hz, 1H), 2.00–2.10 (m, 1H), 2.50–2.63 (m, 2H), 3.92 (s, 3H), 4.07–4.10 (m, 1H), 4.22 (s, 1H), 4.44–4.58 (m, 2H), 5.12 (d, J=17 Hz, 1H), 5.43 (m, 1H), 5.76–5.89 (m, 1H), 7.02–7.23 (m, 7H), 7.35 (m, 1H), 7.45–7.53 (m, 4H), 8.01–8.11 (m, 3H). HRMS calcd. for $C_{48}H_{53}ClN_5O_9S_3$: 974.2694, found 974.2696. LC (retention time: 1.95, Method A).

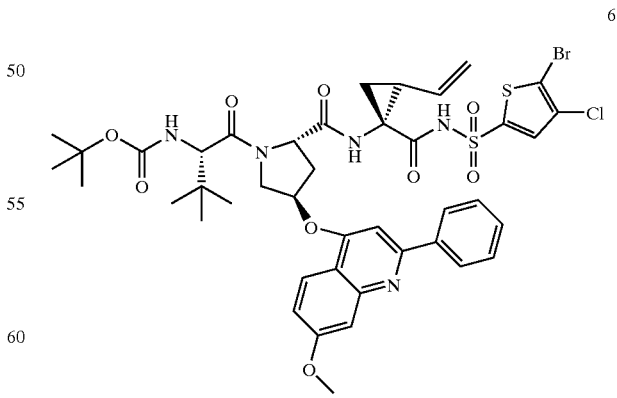

6

Example 8

Compound 6, BOCNH-P3(L-t-BuGly)-P2[(4R)-(2-phenyl-7-methoxyquinoline-4-oxo)-S-proline]-P1(1R,2S VinylAcca)-CONH(2-sulfonyl-4-chloro-5-bromothiophene) or alternate designation, Compound 6, the (1R,2S) P1 isomer of {-[2-{1-[5-Bromo-4-chlorothiophene-2-sulfonylamino-carbonyl]-2-vinylcyclopropylcarbamoyl}-4-(7-methoxy-2-phenyl-quinolin-4-yloxy)pyrrolidine-1-carbonyl]-2,2-dimethylpropyl}carbarmic acid tert-butyl ester, shown above, was prepared in analogous fashion to that of compound 2 but using 5-bromo-4-chloro-thiophene-2-sulfonamide purchased from Maybridge as the primary sulfonamide: $^1$H NMR (methanol-d$_4$, 300 MHz) δ 1.02 (s, 9H), 1.27 (s, 9H), 1.43 (m, 1H), 1.78 (dd, J=8, 5 Hz, 1H), 2.00–2.10 (m, 1H), 2.49–2.58 (m, 1H), 2.69 (dd, J=14, 8 Hz, 1H), 3.91 (s, 3H), 4.09 (m, 1H), 4.22 (s, 1H), 4.47 (d, J=12 Hz, 2H), 4.58 (t, J=9 Hz, 1H), 4.94 (dd, J=10, 2 Hz, 1H), 5.14 (d, J=17 Hz, 1H), 5.48 (m, 1H), 5.78–5.91 (m, 1H), 7.04 (dd, J=9.2, 2.2 Hz, 1H), 7.21 (s, 1H), 7.34–7.40 (m, 2H), 7.44–7.53 (m, 3H), 8.01–8.07 (m, 3H). HRMS calcd. for C$_{42}$H$_{48}$BrClN$_5$O$_9$S$_2$: 944.1765, found 944.1763. LC (retention time: 1.87, Method A).

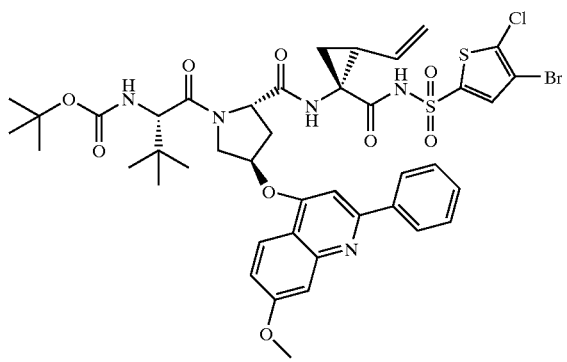

Example 9

Compound 7, BOCNH-P3(L-t-BuGly)-P2[(4R)-(2-phenyl-7-methoxyquinoline-4-oxo)-S-proline]-P1(1R,2S VinylAcca)-CONH(2-sulfonyl-4-bromo-5-chlorothiophene) or alternate designation, Compound 7, the (1R,2S) P1 isomer of {1-[2-{1-[4-Bromo-5-chlorothiophene-2-sulfonylamino-carbonyl]-2-vinylcyclopropylcarbamoyl}-4-(7-methoxy-2-phenyl-quinolin-4-yloxy)pyrrolidine-1-carbonyl]-2,2-dimethylpropyl}carbamic acid tert-butyl ester, shown above, was prepared in analogous fashion to that of compound 2 but using 4-bromo-5-chloro-thiophene-2-sulfonamide purchased from Maybridge as the primary sulfonamide: $^1$H NMR (methanol-d$_4$, 300 MHz) δ 1.02 (s, 9H), 1.27 (s, 9H), 1.43 (m, 1H), 1.78 (dd, J=7.7, 5.1 Hz, 1H), 2.03–2.12 (m, 1H), 2.49–2.59 (m, 1H), 2.66–2.78 (m, 1H), 3.91 (s, 3H), 4.09–4.12 (m, 1H), 4.22 (s, 1H), 4.48 (d, J=11.7 Hz, 1H), 4.56 (t, J=8.6 Hz, 1H), 4.94 (dd, J=10.4, 1.7 Hz, 2H), 5.14 (d, J=17.2 Hz, 1H), 5.48 (m, 1H), 5.79–5.91 (m, 1H), 7.04 (dd, J=9.1, 2.6 Hz, 1H), 7.21 (s, 1H), 7.34–7.55 (m, 5H), 8.01–8.11 (m, 3H). HRMS calcd. for C$_{42}$H$_{48}$BrClN$_5$O$_9$S$_2$: 944.1765, found 944.1763. LC-MS (retention time: 1.88, Method A).

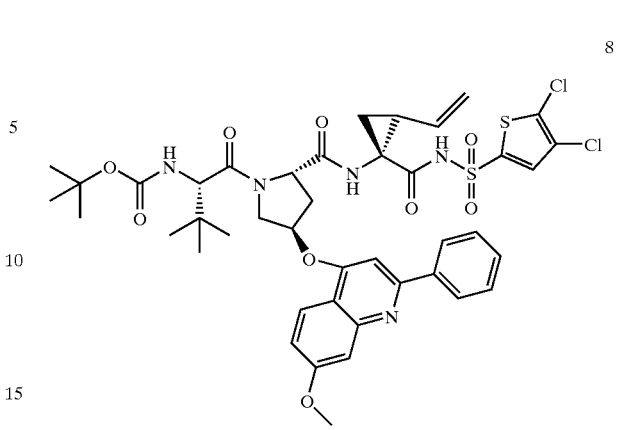

Example 10

Compound 8, BOCNH-P3(L-t-BuGly)-P2[(4R)-(2-phenyl-7-methoxyquinoline-4-oxo)-S-proline]-P1(1R,2S VinylAcca)-CONH(2-sulfonyl-4,5-dichlorothiophene) or alternate designation, Compound 8, the (1R,2S) P1 isomer of {1-[2-{1-[4,5-dichlorothiophene-2-sulfonylaminocarbonyl]-2-vinylcyclopropylcarbamoyl}-4-(7-methoxy-2-phenyl-quinolin-4-yloxy)pyrrolidine-1-carbonyl]-2,2-dimethylpropyl}carbamic acid tert-butyl ester, shown above, was prepared in analogous fashion to that of compound 2 but using 4,5-dichlorothiophene-2-sulfonamide purchased from Maybridge as the primary sulfonamide: $^1$H NMR (methanol-d$_4$, 300 MHz) δ 1.02 (s, 9H), 1.27 (s, 9H), 1.44 (m, 1H), 1.78 (dd, J=7.7, 5.1 Hz, 1H), 2.00–2.12 (m, 1H), 2.51–2.61 (m, 1H), 2.67–2.81 (m, 1H), 3.92 (s, 3H), 4.09–4.13 (m, 1H), 4.22 (s, 1H), 4.48 (d, J=11.3 Hz, 1H), 4.57 (t, J=8.4 Hz, 1H), 4.94 (dd, J=10.4, 2 Hz, 2H), 5.15 (d,d, J=17.2, 1.5 Hz, 1H), 5.50 (m, 1H), 5.78–5.91 (m, 1H), 7.05 (dd, J=9.2, 2.2 Hz, 1H), 7.23 (s, 1H), 7.35–7.41 (m, 2H), 7.47–7.55 (m, 3H), 8.01–8.12 (m, 3H). HRMS cald for C$_{42}$H$_{48}$Cl$_2$N$_5$O$_9$S$_2$: 900.2271, found 900.2285. LC (retention time: 1.86, Method A).

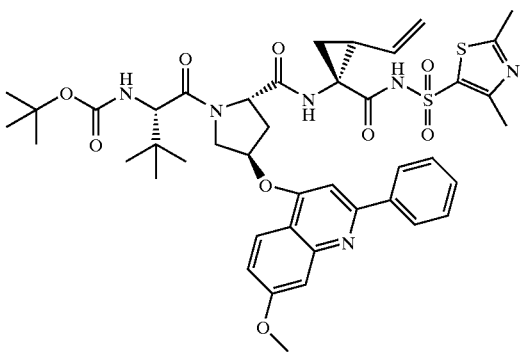

Example 11

Compound 9, BOCNH-P3(L-t-BuGly)-P2[(4R)-(2-phenyl-7-methoxyquinoline-4-oxo)-S-proline]-P1(1R,2S VinylAcca)-CONH(5-sulfonyl-2,4-dimethylthiazole) or alternate designation, Compound 9, the (1R,2S) P1 isomer of {1-[2-{1-[2,4-dimethylthiazole-5-sulfonylaminocarbonyl]-2-vinylcyclopropylcarbamoyl}-4-(7-methoxy-2-phenyl-quinolin-4-yloxy)pyrrolidine-1- carbonyl]-2,2-dimethylpropyl}carbamic acid tert-butyl ester, shown above, was prepared in analogous fashion to that of compound 2 but using 2,4-dimethyl-1,3-thiazole-5-sulfonamide purchased from Maybridge as the primary sulfonamide: HRMS calcd. for $C_{43}H_{53}N_6O_9S_2$: 861.3315, found 861.3340. LC-MS (retention time: 1.64, Method A), MS m/z 861(M$^+$+1).

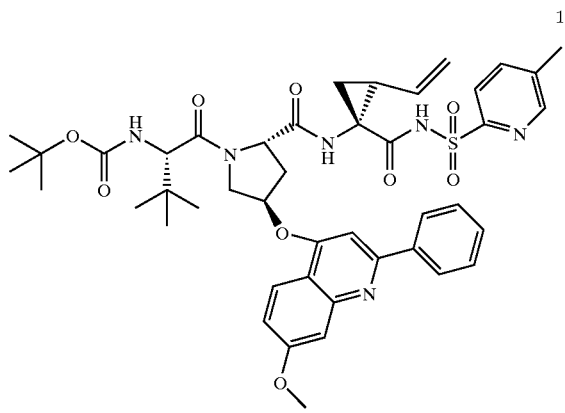

Example 12

Compound 10, BOCNH-P3(L-t-BuGly)-P2[(4R)-(2-phenyl-7-methoxyquinoline-4-oxo)-S-proline]-P1(1R,2S VinylAcca)-CONH(5-methylpyridine-2-sulfonyl) or alternate designation, Compound 10, the (1R,2S) P1 isomer of (1-{4-(7-Methoxy-2-phenyl-quinolin-4-yloxy)-2-[1-(5-methyl-pyridine-2-sulfonylaminocarbonyl)-2-vinylcyclopropylcarbamoyl]pyrrolidine-1-carbonyl}-2,2-dimethylpropyl)carbamic acid tert-butyl ester, shown above, was prepared in analogous fashion to that of compound 2 but using 5-methyl-2-pyridinesulfonamide purchased from Fluka as the primary sulfonamide: $^1$H NMR (methanol-d$_4$, 300 MHz) δ 1.02 (s, 9H), 1.30 (s, 9H), 1.41 (m, 1H), 1.69–1.80 (m, 1H), 2.04–2.12 (m, 1H), 2.22 (s, 3H), 2.33–2.50 (m, 2H), 3.92 (s, 3H), 4.05 (m, 1H), 4.20 (s, 1H), 4.41–4.57 (m, 2H), 4.99–5.23 (m, 1H), 5.43 (m, 1H), 5.78–5.91 (m, 1H), 7.01–7.09 (m, 1H), 7.18 (s, 1H), 7.36–7.39 (m, 1H), 7.45–7.56 (m, 3H), 7.64–7.67 (m, 1H), 7.72–7.79 (m, 1H), 8.03–8.24 (m, 4H). LC-MS (retention time: 1.66, Method D), MS m/z 841 (M$^+$+1).

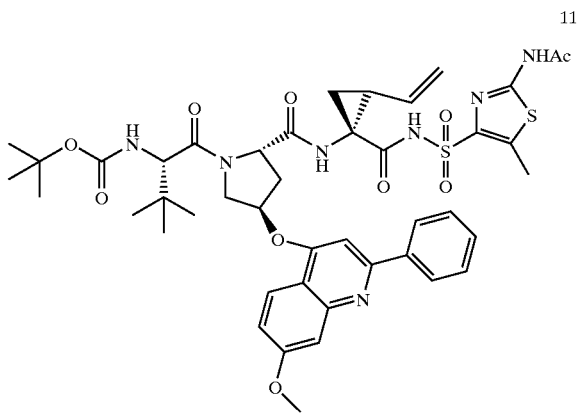

Example 13

Compound 11, BOCNH-P3(L-t-BuGly)-P2[(4R)-(2-phenyl-7-methoxyquinoline-4-oxo)-S-proline]-P1(1R,2S VinylAcca)-CONH(4-sulfonyl-2-acetylamino-5-methylthiazole) or alternate designation, Compound 11, the (1R,2S) P1 isomer of {1-[2-{1-[2-Acetylamino-5-methylthiazole-4-sulfonylaminocarbonyl]-2-vinylcyclopropylcarbamoyl}-4-(7-methoxy-2-phenyl-quinolin-4-yloxy)pyrrolidine-1-carbony]-2,2-dimethylpropyl}carbamic acid tert-butyl ester, shown above, was prepared in analogous fashion to that of compound 2 but using 2-Acetylamino-5-methylthiazole-4-sulfonamide (prepared from 2-Acetylamino-5-methylthiazole-4-sulfonyl chloride purchased from Aldrich and converted to the primary sulfonamide in analogous fashion to the method of Steinkopf and Hoepner, *Justus Liebigs Ann. Chem.*, 501, 1933, p.174–182): $^1$H NMR (methanol-d$_4$, 300 MHz) δ 1.05 (s, 9H), 1.29 (s, 9H), 1.35–1.44 (m, 1H), 1.73–1.80 (m, 1H), 1.92–2.09 (m, 1H), 2.21 (s, 3H), 2.49 (s, 3H), 2.54–2.62 (m, 1H), 2.71–2.79 (m, 1H), 3.95 (s, 3H), 4.11–4.16 (m, 1H), 4.24 (m, 1H), 4.50–4.68 (m, 2H), 4.91–5.01 (m, 1H), 5.17 (d, J=17 Hz, 1H), 5.54 (m, 1H), 5.67–6.01 (m, 1H), 7.08 (dd, J=9, 2 Hz, 1H), 7.26 (s, 1H), 7.40 (d, J=2 Hz, 1H), 7.47–7.57 (m, 3H), 8.02, 8.04 (m, 2H), 8.11 (d, J=9 Hz, 1H); HRMS m/z (M+H)$^+$ calcd for $C_{44}H_{54}N_7S_2O_{10}$: 904.3374, found 904.3374. LC (retention time: 1.59, Method A).

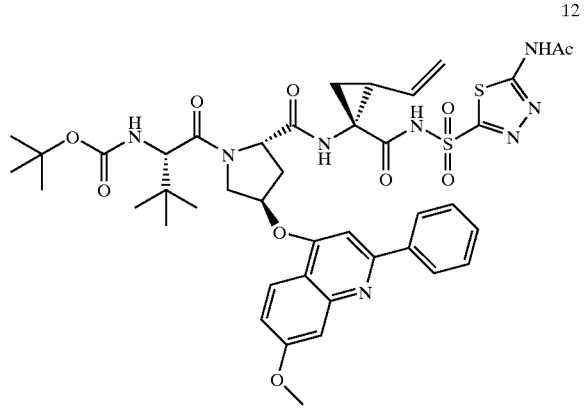

Example 14

Compound 12, BOCNH-P3(L-t-BuGly)-P2[(4R)-(2-phenyl-7-methoxyquinoline-4-oxo)-S-proline]-P1(1R,2S VinylAcca)-CONH(2-sulfonyl-5-Acetylamino-[1,3,4] thiadiazole) or alternate designation, Compound 12, the (1R,2S) P1 isomer of {1-[2-[1-(5-Acetylamino-[1,3,4] thiadiazole-2-sulfonylaminocarbonyl)-2-vinylcyclopropylcarbamoyl]-4-(7-methoxy-2-phenyl-quinolin-4-yloxy)-pyrrolidine-1-carbonyl]-2,2-dimethylpropyl}carbamic acid tert-butyl ester, shown below, was prepared in analogous fashion to that of compound 2 but using acetazolamide purchased from Aldrich as the primary sulfonamide: $^1$H NMR (methanol-d$_4$, 300 MHz) δ 1.03 (s, 9H), 1.27 (s, 9H), 1.43 (m, 1H), 1.64–2.10 (m, 2H), 2.19 (s, 3H), 2.44–2.89 (m, 2H), 3.93 (s, 3H), 4.12–4.24 (m, 2H), 4.49 (d, J=12 Hz, 1H), 4.55–4.61 (m, 1H), 5.11 (d, J=17 Hz, 1H), 5.55 (m, 1H), 5.72–5.87 (m, 1H), 7.05–7.14 (m, 1H), 7.26 (s, 1H), 7.37 (m, 1H), 7.44–7.58 (m, 3H), 7.97–8.13 (m, 3H); HRMS m/z (M+H)$^+$ calcd. for $C_{42}H_{51}N_8S_2O_{10}$: 891.3170, found 891.3152. LC-MS (retention time: 1.58, Method A), MS m/z 891(M$^+$+1).

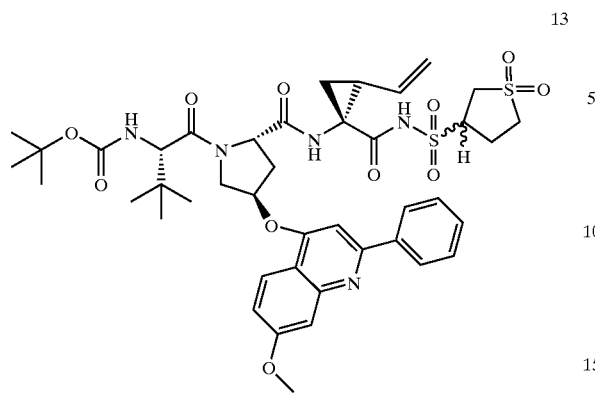

13

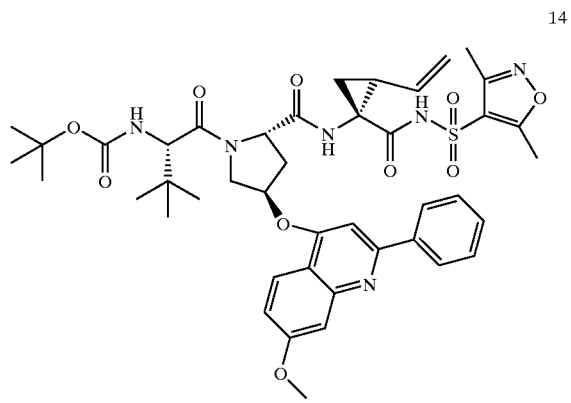

14

Example 15

Compound 13, BOCNH-P3(L-t-BuGly)-P2[(4R)-(2-phenyl-7-methoxyquinoline-4-oxo)-S-proline]-P1 (1R,2S VinylAcca)-CONH(1,1-Dioxo-tetrahydro-1H-1☐6-thiophene-3(R/S)-sulfonylaminocarbonyl) or alternate designation, Compound 13, the (1R,2S) P1 isomer of {1-[2-[1-(1,1-Dioxo-tetrahydro-1H-1☐6-thiophene-3(R/S)-sulfonylaminocarbonyl)-2-vinylcyclopropylcarbamoyl]-4-(7-methoxy-2-phenyl-quinolin-4-yloxy)pyrrolidine-1-carbonyl]-2,2-dimethylpropyl}carbamic acid tert-butyl ester, shown above, was prepared in analogous fashion to that of compound 2 but using 1,1-Dioxo-tetrahydro-1H-1☐6-thiophene-3(R/S)-sulfonamide purchased from Maybridge as the primary sulfonamide: $^1$H NMR (methanol-d$_4$, 300 MHz) δ 1.04 (s, 9H), 1.29 (s, 9H), 1.44 (m, 1H), 1.72–1.80 (m, 1H), 2.01–2.10 (m, 1H), 2.43–2.64 (m, 3H), 2.69–2.76 (m, 1H), 3.04–3.52 (m, 4H), 3.92 (s, 3H), 3.97–4.11 (m, 2H), 4.24 (s, 1H), 4.48–4.60 (m, 2H), 5.01 (d, J=12 Hz, 1H), 5.18 (d, J=17 Hz, 1H), 5.50 (m, 1H), 5.85–6.00 (m, 1H), 7.03–7.10 (m, 1H), 7.24 (s, 1H), 7.36 (m, 1H), 7.45–7.55 (m, 3H), 8.03–8.12 (m, 3H); HRMS m/z (M+H)$^+$ calcd for $C_{42}H_{54}N_5S_2O_{11}$: 868.3261, found 868.3256. LC-MS (retention time: 1.48, Method A), MS m/z 868(M$^+$+1).

Example 16

Compound 14, BOCNH-P3(L-t-BuGly)-P2[(4R)-(2-phenyl-7-methoxyquinoline-4-oxo)-S-proline]-P1(1R,2S VinylAcca)-CONH(-(3,5-Dimethylisoxazole-4-sulfonyl) or alternate designation, Compound 14, the (1R,2S) P1 isomer of {1-[2-[1-(3,5-Dimethylisoxazole-4-sulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester, shown above, was prepared in analogous fashion to that of compound 2 but using 3,5-dimethylisoxazole-4-sulfonamide purchased from Maybridge as the primary sulfonamide: $^1$H NMR (methanol-d$_4$, 300 MHz) δ 1.04 (s, 9H), 1.26 (s, 9H), 1.43 (m, 1H), 1.68–1.79 (m, 1H), 1.95–2.06 (m, 1H), 2.35 (s, 3H), 2.58 (s, 3H), 2.50–2.60 (m, 1H), 2.66–2.73 (m, 1H), 3.94 (s, 3H), 4.08–4.16 (m, 1H), 4.23 (s, 1H), 4.50–4.57 (m, 2H), 4.91–4.95 (m, 1H), 5.11–5.19 (m, 1H), 5.48 (m, 1H), 5.48–5.77 (m, 1H), 7.05–7.14 (m, 1H), 7.26 (m, 1H), 7.39 (m, 1H), 7.46–7.57 (m, 3H), 8.05–8.13 (m, 3H); HRMS m/z (M+H)$^+$ calcd. for $C_{43}H_{53}N_6SO_{10}$: 845.3544, found 845.3541. LC-MS (retention time: 1.66, Method A), MS m/z 845(M$^+$+1).

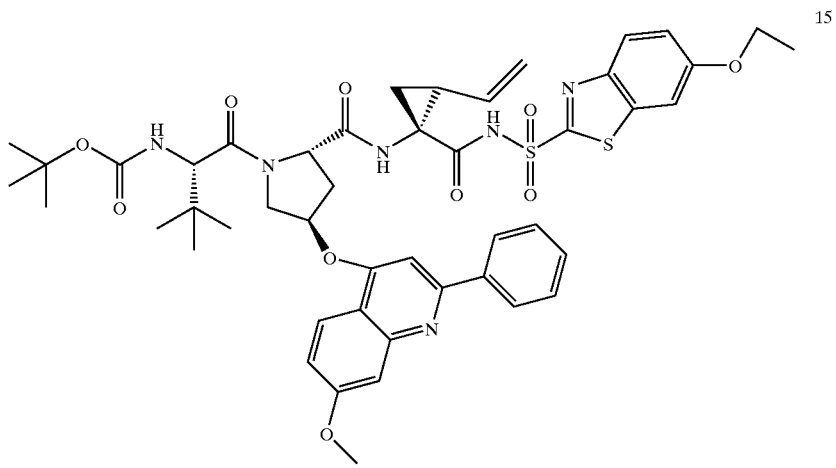

15

Example 17

Compound 15, BOCNH-P3(L-t-BuGly)-P2[(4R)-(2-phenyl-7-methoxyquinoline-4-oxo)-S-proline]-P1(1R,2S VinylAcca)-CONH(6-Ethoxybenzothiazole-2-sulfonyl) or alternate designation, Compound 15, the (1R,2S) P1 isomer of {1-[2-[1-(6-Ethoxybenzothiazole-2-sulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethylpropyl}-carbamic acid tert-butyl ester, shown above, was prepared in analogous fashion to that of compound 2 but 6-Ethoxy-2-benzothiazolesulfonamide purchased from Aldrich as the primary sulfonamide: $^1$H NMR (methanol-$d_4$, 300 MHz) δ 1.01 (s, 9H), 1.28 (s, 9H), 1.25–1.37 (m, 4H), 1.76 (dd, J=7.5, 4.9 Hz, 1H), 2.00–2.22 (m, 2H), 2.35 (m, 1H), 3.83–4.06 (m, 3H), 3.93 (s, 3H), 4.19 (s, 1H), 4.34–4.55 (m, 2H), 5.10 (d, J=17.2 Hz, 1H), 5.43 (m, 1H), 5.79–5.99 (m, 1H), 6.79–6.88 (m, 1H), 7.02–7.14 (m, 2H), 7.21 (s, 1H), 7.37 (m, 1H), 7.43–7.56 (m, 4H), 7.98–8.08 (m, 3H). HRMS calcd. for $C_{47}H_{55}N_6O_{10}S_2$ 927.3421 found 927.3427. LC (retention time: 1.80, Method A).

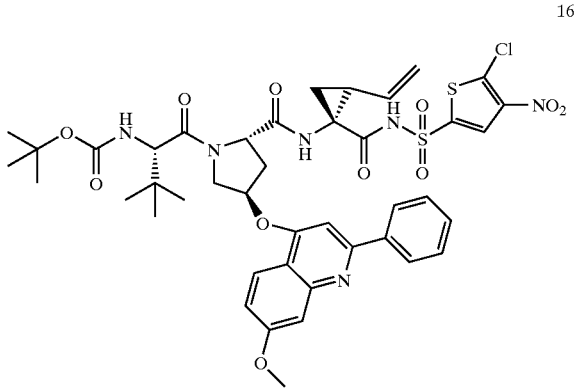

Example 18

Compound 16, BOCNH-P3(L-t-BuGly)-P2[(4R)-(2-phenyl-7-methoxyquinoline-4-oxo)-S-proline]-P1(1R,2S VinylAcca)-CONH(5-Chloro-4-nitrothiophene-2-sulfonyl) or alternate designation, Compound 16, the (1R,2S) P1 isomer of {1-[2-[1-(5-Chloro-4-nitro-thiophene-2-sulfonylaminocarbonyl)-2-vinylcyclopropylcarbamoyl]-4-(7-methoxy-2-phenyl-quinolin-4-yloxy)-pyrrolidine-1-carbonyl]-2,2-dimethyl-propyl}carbamic acid tert-butyl ester, shown above, was prepared in analogous fashion to that of compound 2 but using 5-Chloro-4-nitrothiophene-2-sulfonamide purchased from Buttpark as the primary sulfonamide: HRMS calcd. for $C_{42}H_{48}ClN_6O_{11}S_2$: 911.2511, found 911.2494. LC (retention time: 1.75, Method A).

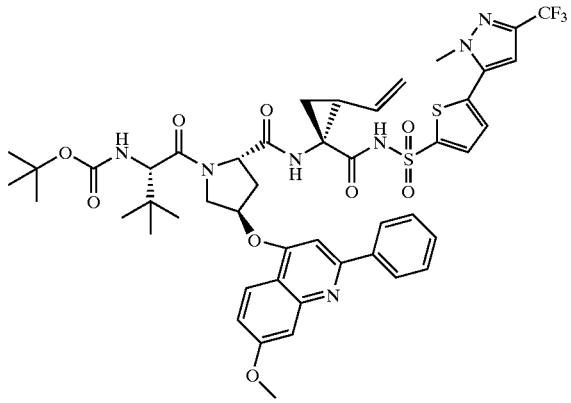

Example 19

Compound 17, BOCNH-P3(L-t-BuGly)-P2[(4R)-(2-phenyl-7-methoxyquinoline-4-oxo)-S-proline]-P1(1R,2S VinylAcca)-CONH(5-(2-methyl-5-trifluoromethyl-2H-pyrazol-3-yl)thiophene-2-sulfonyl) or alternate designation, Compound 17, the (1R,2S) P1 isomer of [1-(4-(7-Methoxy-2-phenyl-quinolin-4-yloxy)-2-{1-[5-(2-methyl-5-trifluoromethyl-2H-pyrazol-3-yl)thiophene-2-sulfonylaminocarbonyl]-2-vinyl-cyclopropylcarbamoyl}-pyrrolidine-1-carbonyl)-2,2-dimethylpropyl]carbamic acid tert-butyl ester, shown above, was prepared in analogous fashion to that of compound 2 but using 5-(2-methyl-5-trifluoromethyl-2H-pyrazol-3-yl)thiophene-2-sulfonamide purchased from Buttpark as the primary sulfonamide: $^1$H NMR (methanol-$d_4$, 300 MHz) δ 1.02 (s, 9H), 1.26 (s, 9H), 1.42 (m, 1H), 1.78 (dd, J=7.7, 5.1 Hz, 1H), 2.10 (q, J=8.8 Hz, 2H), 2.55–2.70 (m, 2H), 3.84–4.00 (m, 6H), 4.12 (m, 1H), 4.22 (m, 1H), 4.45–4.59 (m, 2H), 4.91 (d, J=12 Hz, 1H), 5.14 (d, J=16.8 Hz, 1H), 5.48 (s, 1H), 5.82–5.94 (m, 1H), 6.70 (m, 1H), 7.02–7.07 (m, 1H), 7.17–7.21 (m, 2H), 7.34 (m, 1H), 7.44–7.53 (m, 3H), 7.61 (d, J=4.0 Hz, 1H), 8.00–8.11 (m, 3H). HRMS cald for $C_{47}F_3H_{53}N_7O_9S_2$ 980.3298 found 980.3308. LC (retention time: 1.78, Method A).

Example 20

Preparation of additional P1 Intermediates for incorporation in compounds of Fomula I.

The P1 intermediates described in this section can be used to prepare compounds of Formula I by the methods described herein.

1. Resolution of N-Boc-(1R,2S)/(1S,2R)-1-amino-2-vinylcyclopropane carboxylic acid ethyl ester

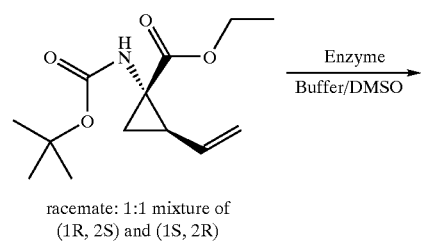

racemate: 1:1 mixture of (1R, 2S) and (1S, 2R)

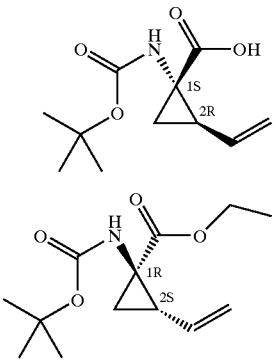

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Acalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee")).

The aqueous layer from the extraction process was then acidified to pH 2 with 50% H$_2$SO$_4$ and extracted with MTBE (2×2 L). The MTBE extract was washed with water (3×100 mL) and evaporated to give the acid as light yellow solid (42.74 g; purity: 99% @ 210 nm, containing no ester).

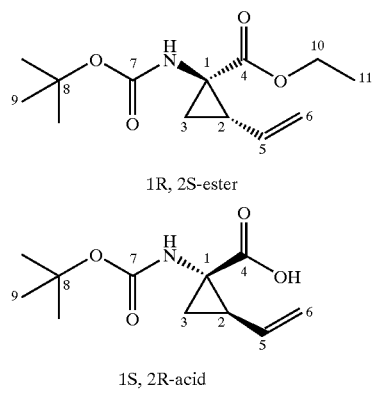

1R, 2S-ester 1S, 2R-acid

| | ester | acid |
|---|---|---|
| High Resolution Mass Spec | (+) ESI, C13H22NO4, [M + H]$^+$, cal. 256.1549, found 256.1542 | (−) ESI, C11H16NO4, [M − H]$^−$, cal. 226.1079, found 226.1089 |

NMR observed chemical shift
Solvent: CDCl$_3$ (proton δ 7.24 ppm, C-13 δ 77.0 ppm)
Bruker DRX-500C: proton 500.032 Mhz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10(q, J = 9.0Hz) | 34.1 | 2.17(q, J = 9.0Hz) | 35.0 |
| 3a | 1.76(br) | 23.2 | 1.79(br) | 23.4 |
| 3b | 1.46(br) | | 1.51, (br) | |
| 4 | — | 170.8 | — | 175.8 |
| 5 | 5.74(ddd, J = 9.0, 10.0, 17.0Hz) | 133.7 | 5.75(m) | 133.4 |
| 6a | 5.25(d, J = 17.0Hz) | 117.6 | 5.28(d, J = 17.0Hz) | 118.1 |
| 6b | 5.08(dd, J = 10.0, 1.5Hz) | | 5.12(d, J = 10.5Hz) | |
| 7 | — | 155.8 | — | 156.2 |
| 8 | — | 80.0 | — | 80.6 |
| 9 | 1.43(s) | 28.3 | 1.43(s) | 28.3 |
| 10 | 4.16(m) | 61.3 | — | — |
| 11 | 1.23(t, J = 7.5Hz) | 14.2 | — | — |

Resolution B

To 0.5 mL 100 mM Heps•Na buffer (pH 8.5) in a well of a 24 well plate (capacity: 10 ml/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("μl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Resolution C

To 0.5 ml 100 mM Heps•Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 μl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Samples analysis was carried out in the following manner:
1) Sample preparation: About 0.5 ml of the reaction mixture was mixed well with 10 volume of EtOH. After centrifugation, 10 μl of the supernatant was injected onto HPLC column.
2) Conversion determination:
Column: YMC ODS A, 4.6×50 mm, S-5 μm
Solvent: A, 1 mM HCl in water; B, MeCN
Gradient: 30% B for 1 min; 30% to 45% B over 0.5 min; 45% B for 1.5 min; 45% to 30% B over 0.5 min.
Flow rate: 2 ml/min
UV Detection: 210 nm
Retention time: acid, 1.2 min; ester, 2.8 min.
3) Enantio-excess determination for the ester:
Column: CHIRACEL OD-RH, 4.6×150 mm, S-5 μm
Mobile phase: MeCN/50 mM HClO$_4$ in water (67/33)
Flow rate: 0.75 ml/min.
UV Detection: 210 nm.
Retention time:
(1S,2R) isomer as acid: 5.2 min;
Rcaemate: 18.5 min and 20.0 min;
(1R,2S) isomer as ester: 18.5 min.

2. Preparation of N-Boc-(1R,2S)-1-amino-2-cyclopropylcyclopropane carboxylic acid ethyl ester

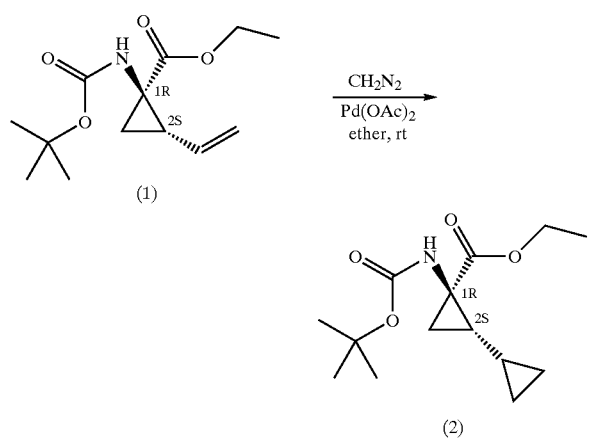

A solution of N-Boc-(1R,2S)-1-amino-2-vinylcyclopropane carboxylic acid (255 mg, 1.0 mmol) in ether (10 mL) was treated with palladium acetate (5 mg, 0.022 mmol). The orange/red solution was placed under an atmosphere of N$_2$. An excess of diazomethane in ether was added dropwise over the course of 1 h. The resulting solution was stirred at rt for 18 h. The excess diazomethane was removed using a stream of nitrogen. The resulting solution was concentrated by rotary evaporation to give the crude product. Flash chromatography (10% EtOAc/hexane) provided 210 mg (78%) of N-Boc-(1R,2S)-1-amino-2-cyclopropylcyclopropane carboxylic acid ethyl ester as a colorless oil. LC-MS (retention time: 2.13, similar to method A except: gradient time 3 min, Xterra MS C18 S7 3.0×50 mm column), MS m/e 270 (M$^+$+1).

3. 1-tert-butoxycarbonylamino-cyclopropane-carboxylic acid is commercially available

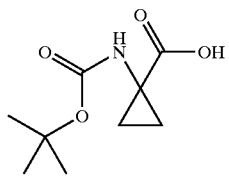

4. Preparation of 1-aminocyclobutanecarboxylic acid methyl ester-hydrochloride

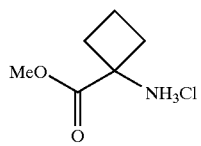

1-aminocyclobutanecarboxylic acid (100 mg, 0.869 mmol) (Tocris) was dissolved in 10 mL of MeOH, HCl gas was bubbled in for 2 h. The reaction mixture was stirred for 18 h, and then concentrated in vacuo to give 144 mg of a yellow oil. Trituration with 10 mL of ether provided 100 mg of the titled product as a white solid. $^1$H NMR (CDCl$_3$) δ 2.10–2.25 (m, 1H), 2.28–2.42 (m, 1H), 2.64–2.82 (m, 4H), 3.87 (s, 3H), 9.21 (br s, 3H).

5. Preparation of racemic (1R,2R)/(1S,2S) 1-Amino-2-ethylcyclopropanecarboxylic acid tert-butyl ester, shown below.

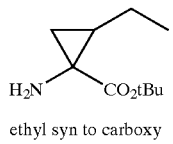

ethyl syn to carboxy

Step 1: Preparation of 2-Ethylcyclopropane-1,1-dicarboxylic acid di-tert-butyl ester, shown below.

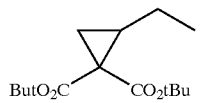

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred 18 h at rt, a mixture of ice and water was then added. The crude product was extracted with CH$_2$Cl$_2$ (3×) and sequentially washed with water (3×), brine and the organic extracts combined. The organic layer was dried (MgSO$_4$), filtered and concentrated in vacuo. The resulting residue was flash chromatographed (100 g SiO$_2$, 3% Et$_2$O in hexane) to afford the titled product (18.3 g, 67.8 mmol, 73% yield) which was used directly in the next reaction.

Step 2: Preparation of racemic 2-Ethylcyclopropane-1,1-dicarboxylic acid tert-butyl ester, shown below.

The product of Step 1 (18.3 g, 67.8 mmol) was added to a suspension of potassium tert-butoxide (33.55 g, 299.0 mmol) in dry ether (500 mL) at 0° C., followed by H$_2$O (1.35 mL, 75.0 mmol) and was vigorously stirred overnight at rt. The reaction mixture was poured in a mixture of ice and water and washed with ether (3×). The aqueous layer was acidified with a 10% aq. citric acid solution at 0° C. and extracted with EtOAc (3×). The combined organic layers were washed with water (2×), brine, dried (MgSO$_4$) and concentrated in vacuo to afford the titled product as a pale yellow oil (10 g, 46.8 mmol, 69% yield).

Step 3: Preparation of (1R,2R)/(1S,2S) 2-Ethyl-1-(2-trimethylsilanylethoxycarbonylamino)cyclopropanecarboxylic acid tert-butyl ester, shown below.

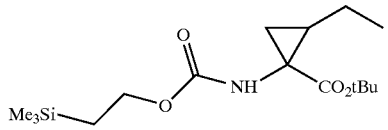

To a suspension, of the product of Step 2 (10 g, 46.8 mmol) and 3 g of freshly activated 4A molecular sieves in dry benzene (160 mL), was added Et$_3$N (7.50 mL, 53.8 mmol) and DPPA (11 mL, 10.21 mmol). The reaction mixture was refluxed for 3.5 h, 2-trimethylsilyl-ethanol (13.5 mL, 94.2 mmol) was then added, and the reaction mixture was refluxed overnite. The reaction mixture was filtered, diluted with Et$_2$O, washed with a 10% aqueous citric acid solution, water, saturated aqueous NaHCO$_3$, water (2×), brine (2×), dried (MgSO$_4$) and concentrated in vacuo. The residue was suspended with 10 g of Aldrich polyisocyanate scavenger resin in 120 mL of CH$_2$Cl$_2$, stirred at rt overnite and filtered to afford the titled product (8 g, 24.3 mmol; 52%) as a pale yellow oil: $^1$H NMR (CDCl$_3$) δ 0.03 (s, 9H), 0.97 (m, 5H), 1.20 (bm, 1H), 1.45 (s, 9H), 1.40–1.70 (m, 4H), 4.16 (m, 2H), 5.30 (bs, 1H).

Step 4: Preparation of racemic (1R,2R)/(1S,2S) 1-Amino-2-ethylcyclopropanecarboxylic acid tert-butyl ester, shown below.

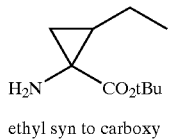

ethyl syn to carboxy

To the product of Step 3 (3 g, 9 mmol) was added a 1.0 M TBAF solution in THF (9.3 mL, 9.3 mmol) and the mixture heated to reflux for 1.5 h, cooled to rt and then diluted with 500 ml of EtOAc. The solution was successively washed with water (2×100 mL), brine (2×100 mL), dried (MgSO$_4$), concentrated in vacuo to provide the title intermediate 6. Preparation of 1-Amino-spiro[2.3]hexane-1-carboxylic acid methyl ester hydrochloride salt

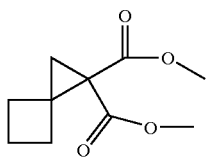

Step 1 Preparation of [2,3]hexane-1,1-dicarboxylic acid dimethyl ester, shown below.

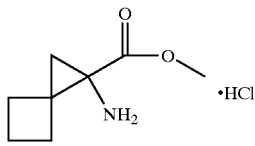

To a mixture of methylene-cyclobutane (1.5 g, 22 mmol) and Rh$_2$(OAc)$_4$ (125 mg, 0.27 mmol) in anhydrous CH$_2$Cl$_2$ (15 mL) was added 3.2 g (20 mmol) of dimethyl diazomalonate (prepared according to J. Lee et al. *Synth. Comm.*, 1995, 25, 1511–1515) at 0° C. over a period of 6 h. The reaction mixture was then warmed to rt and stirred for another 2 h. The mixture was concentrated and purified by flash chromatography (eluting with 10:1 hexane/Et$_2$O to 5:1 hexane/Et$_2$O) to give 3.2 g (72%) of [2,3]hexane-1,1-dicarboxylic acid dimethyl ester as a yellow oil. $^1$H NMR (300 MHz, CDCl$_3$) δ 3.78 (s, 6H), 2.36 (m, 2H), 2.09 (m, 3H), 1.90 (m, 1H), 1.67 (s, 2H). LC-MS: MS m/z 199 (M$^+$+1).

Step 2: Preparation of spiro[2,3]hexane-1,1-dicarboxylic acid methyl ester, shown below.

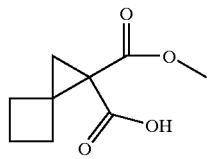

To the mixture of spiro [2,3]hexane-1,1-dicarboxylic acid dimethyl ester (200 mg, 1.0 mmol) in 2 mL of MeOH and 0.5 mL of water was added KOH (78 mg, 1.4 mmol). This solution was stirred at rt for 2 days. It was then acidified with dilute HCl and extracted two times with ether. The combined organic phases were dried (MgSO$_4$) and concentrated to yield 135 mg (73%) of 2 as a white solid. $^1$H NMR (300 MHz, CDCl$_3$) δ 3.78 (s, 3H), 2.36–1.90 (m, 8H). LC-MS: MS m/z 185 (M$^+$+1)

Step 3: Preparation of the titled product, 1-amino-spiro[2.3]hexane-1-carboxylic acid methyl ester hydrochloride salt.

To a mixture of spiro[2,3]hexane-1,1-dicarboxylic acid methyl ester (660 mg, 3.58 mmol) in 3 mL of anhydrous t-BuOH was added 1.08 g (3.92 mmol) of DPPA and 440 mg (4.35 mmol) of Et$_3$N. The mixture was heated at reflux for 21 h and then partitioned between H$_2$O and ether. The ether phase was dried over magnesium sulfate, filtered and concentrated in vacuo to yield an oil. To this oil was added 3 mL of a 4 M HCl/dioxane solution. This acidic solution was stirred at rt for 2 h and then concentrated in vacuo. The residue was triturated with ether to give 400 mg (58%) of desried prodict as a white solid. $^1$H NMR (300 MHz, d$_6$-DMSO) δ 8.96 (br s, 3H), 3.71 (s, 3H), 2.41 (m, 1H), 2.12 (m, 4H), 1.93 (m, 1H), 1.56 (q, 2H, J=8 Hz). LC-MS of free amine: MS m/z 156 (M$^+$+1).

7. Preparation of 1-Amino-spiro[2.4]heptane-1-carboxylic acid methyl ester hydrochloride salt, shown below, was prepared as follows.

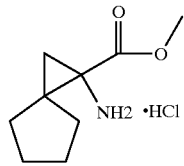

Step 1: Spiro[2.4]heptane-1,1-dicarboxylic acid dimethyl ester, shown below, was prepared as follows.

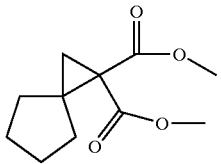

Using the same procedure described in the preparation of 1-Amino-spiro[2.3]hexane-1-carboxylic acid methyl ester hydrochloride salt 1.14 g (13.9 mmol) of methylenecyclopentane and 2.0 g (12.6 mmol) of dimethyl diazomalonate were reacted to yield 1.8 g (67%) of the dimethyl ester. $^1$H NMR (300 MHz, CDCl$_3$) δ 3.73 (s, 6H), 1.80 (m, 2H), 1.70 (m, 4H), 1.60 (m, 4H). LC-MS: MS m/z 213 (M$^+$+1).

Step 2: Preparation of Spiro[2.4]heptane-1,1-dicarboxylic acid methyl ester, shown below, was prepared as follows.

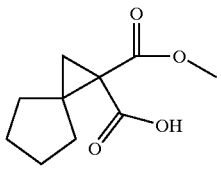

Using the same procedure described in the preparation of 1-Amino-spiro[2.3]hexane-1-carboxylic acid methyl ester hydrochloride salt 1.7 g (8.0 mmol) of the produc of Step 1 and 493 mg (8.8 mmol) of KOH gave 1.5 g (94%) of spiro[2.4]heptane-1,1-dicarboxylic acid methyl ester. $^1$H NMR (300 MHz, CDCl$_3$) δ 3.80 (s, 3H), 2.06 (d, 1H, J=5 Hz), 1.99 (d, 1H, J=5 Hz), 1.80–1.66 (m, 8H). LC-MS: MS m/z 199 (M$^+$+1).

Step 3: Preparation of 1-Amino-spiro[2.4]heptane-1-carboxylic acid methyl ester hydrochloride salt, shown below, was prepared as follows.

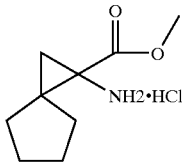

Using the same procedure described above in preparation of 1-Amino-spiro[2.3]hexane-1-carboxylic acid methyl ester hydrochloride salt, 500 mg (2.5 mmol) of the product of Step 2, 705 mg (2.5 mmol) of DPPA and 255 mg (2.5 mmol) of Et$_3$N gave 180 mg (35%) of this hydrochloride salt. $^1$H NMR (300 MHz, d$_6$-DMSO) δ 8.90 (br s, 3H), 3.74 (s, 3H), 1.84 (m, 1H), 1.69 (m, 4H), 1.58 (m, 4H), 1.46 (d, 1H, J=6 Hz). LC-MS of free amine: MS m/z 170 (M$^+$+1).

8. Preparation of 1-Amino-spiro[2.2]pentane-1-carboxylic acid methyl ester hydrochloride salt, shown below, was prepared as follows.

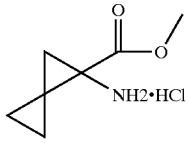

Step 1: Spiro[2.2]pentane-1,1-dicarboxylic acid dimethyl ester, shown below, was prepared as follows.

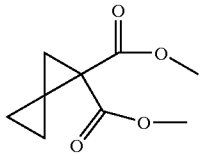

To a mixture of methylenecyclopropane (1.0 g, 18.5 mmol) (prepared according to P. Binger U.S. Pat. No. 5,723,714) and Rh$_2$(OAc)$_4$ (82 mg, 0.185 mmol) in anhydrous CH$_2$Cl$_2$ (10 mL), was added dimethyl diazomalonate (2.9 g, 18.3 mmol) at 0° C. At the top of the flask was installed a cold finger, the temperature of which was kept at −10° C. The reaction mixture was warmed to rt and stirred for another 2 h. The mixture was concentrated in vacuo and purified by flash chromatography (eluting with 10:1 hexane/Et$_2$O to 5:1 hexane/Et$_2$O) to give 0.85 g (25%) of the dimethyl ester as a yellow oil. $^1$H NMR (300 MHz, CDCl$_3$) δ 3.73 (s, 6H), 1.92 (s, 2H), 1.04 (d, 4H, J=3 Hz).

Step 2: Spiro[2.2]pentane-1,1-dicarboxylic acid methyl ester, shown below, was prepared as follows.

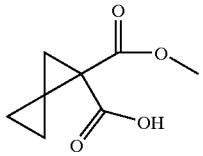

Using the same procedure described above in preparation of 1-Amino-spiro[2.3]hexane-1-carboxylic acid methyl ester hydrochloride salt, 800 mg (4.3 mmol) of the product of step 1 and 240 mg (4.3 mmol) of KOH gave 600 mg (82%) of Spiro[2.2]pentane-1,1-dicarboxylic acid methyl ester. $^1$H NMR (300 MHz, CDCl$_3$) δ 3.82 (s, 6H), 2.35 (d, 1H, J=3 Hz), 2.26 (d, 1H, J=3 Hz), 1.20 (m, 1H), 1.15 (m, 1H), 1.11 (m, 1H), 1.05 (m, 1H). LRMS: MS m/z 169 (M$^+$−1) (Method D).

Step 3: 1-Amino-spiro[2.2]pentane-1-carboxylic acid methyl ester hydrochloride salt, shown below, was prepared as follows.

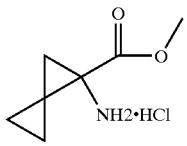

Using the same procedure described above for the preparation of 1-Amino-spiro[2.3]hexane-1-carboxylic acid methyl ester hydrochloride salt, 400 mg (2.3 mmol) of the product of step 2, 700 mg (2.5 mmol) of DPPA and 278 mg (2.7 mmol) of Et$_3$N gave 82 mg (20%) of the hydrochloride salt. $^1$H NMR (300 MHz, CDCl$_3$) δ 9.19 (br s, 3H), 3.81 (s, 3H), 2.16, (d, J=5.5 Hz, 1H), 2.01 (d, J=5.5 Hz, 1H), 1.49 (m, 1H), 1.24, (m, 1H), 1.12 (m, 2H). LRMS of free amine: MS m/z 142 (M$^+$+1).

9. Preparation of 5-Amino-spiro[2.3]hexane-5-carboxylic acid ethyl ester, shown below, was prepared as follows.

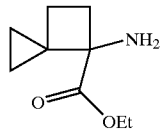

Spiro[2.3]hexan-4-one (500 mg, 5 mmol), which was prepared from bicyclopropylidene (A. Meijere et al. *Org. Syn.* 2000, 78, 142–151) according to A. Meijere et al. *J. Org. Chem.* 1988, 53, 152–161, was combined with ammonium carbamate (1.17 g, 15 mmol) and potassium cyanide (812 mg, 12.5 mmol) in 50 mL of EtOH and 50 mL of water. The mixture was heated at 55° C. for 2 days. Then NaOH (7 g, 175 mmol) was added and the solution was heated under reflux overnight. The mixture was then chilled to 0° C., acidified to pH 1 with concentrated HCl, and concentrated in vacuo. EtOH was added to the crude amino acid mixture and then concentrated to dryness (5×) so as to remove residual water. The residue dissolved in 100 mL of EtOH was cooled to 0° C. It was then treated with 1 mL of $SOCl_2$ and refluxed for 3 days. The solids were removed by filtration, and the filtrate was concentrated in vacuo to give the crude product. The crude product was partitioned between 3 N NaOH, NaCl and EtOAc. The organic phase was dried over potassium carbonate and concentrated. The residue was purified using column chromatography on C18 silica gel (eluting with MeOH/$H_2O$) to yield 180 mg (21%) of 15 as an oil. $^1$H NMR (300 MHz, $CDCl_3$) δ 8.20 (br s, 2H), 4.27 (s, 2H), 2.80 (s, 1H), 2.54 (s, 1H), 2.34 (m, 2H), 1.31 (s, 3H), 1.02 (s, 1H), 0.66 (m, 3H). $^{13}$C NMR (300 MHz, $CDCl_3$) δ 170.2 (s), 63.0 (s), 62.8 (s), 26.1 (s), 26.0 (s), 24.9 (s), 13.9 (s), 11.4 (s), 10.9 (s). LC-MS: MS m/z 170 (M$^+$+1).

Example 21

Biological Studies
Recombinant HCV NS3/4A Protease Complex FRET Peptide Assay

The purpose of this in vitro assay was to measure the inhibition of HCV NS3 protease complexes, derived from the BMS, H77C or J4l6S strains, as described below, by compounds of the present invention. This assay provides an indication of how effective compounds of the present invention would be in inhibiting HCV proteolytic activity.

Serum from an HCV-infected patient was obtained from Dr. T. Wright, San Francisco Hospital. An engineered full-length cDNA template of the HCV genome (BMS strain) was constructed from DNA fragments obtained by reverse transcription-PCR (RT-PCR) of serum RNA and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2–5B, was shown to be >97% identical to HCV genotype 1a (H77C) and 87% identical to genotype 1b (J4 L6S). The infectious clones, H77C (1a genotype) and J4 L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16),8738–8743 (1997); AF054247, see Yanagi, M., St Claire, M., Shapiro, M., Emerson, S. U., Purcell, R. H. and Bukh, J, Virology 244 (1), 161–172. (1998)).

The BMS, H77C and J4 L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620–32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J Virol. 72(8): 6758–69 (1998)) with modifications. Briefly, NS3/4A expression was induced with 0.5 mM Isopropyl β-D-1-thiogalactopyranoside (IPTG) for 22 hr at 20° C. A typical fermentation (10 L) yielded approximately 80 g of wet cell paste. The cells were resuspended in lysis buffer (10 mL/g) consisting of 25 mM N-(2-Hydroxyethyl)Piperazine-N'-(2-Ethane Sulfonic acid) (HEPES), pH7.5, 20% glycerol, 500 mM Sodium Chloride (NaCl), 0.5% Triton-X100, 1 ug/ml lysozyme, 5 mM Magnesium Chloride ($MgCl_2$), 1 ug/ml DnaseI, 5 mM β-Mercaptoethanol (βME), Protease inhibitor—Ethylenediamine Tetraacetic acid (EDTA) free (Roche), homogenized and incubated for 20 mins at 4° C. The homogenate was sonicated and clarified by ultra-centrifugation at 235000 g for 1hr at 4° C. Imidazole was added to the supernatant to a final concentration of 15 mM and the pH adjusted to 8.0. The crude protein extract was loaded on a Nickel—Nitrilotriacetic acid (Ni—NTA) column pre-equilibrated with buffer B (25 mM HEPES, pH8.0, 20% glycerol, 500 mM NaCl, 0.5% Triton-X100, 15 mM imidazole, 5 mM βME). The sample was loaded at a flow rate of 1 mL/min. The column was washed with 15 column volumes of buffer C (same as buffer B except with 0.2% Triton-X100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH7.5, 20% glycerol, 300 mM NaCl, 0.2% Triton-X100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77C and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay, was RET S1 (Resonance Energy Transfer Depsipeptide Substrate; AnaSpec, Inc. cat # 22991) (FRET peptide), described by Taliani et al. in Anal. Biochem. 240(2):60–67 (1996). The sequence of this peptide is loosely based on the NS4A/NS4B natural cleavage site except there is an ester linkage rather than an amide bond at the cleavage site. The peptide substrate was incubated with one of the three recombinant NS3/4A complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad. Assay buffer: 50 mM HEPES, pH7.5; 0.15M NaCl; 0.1% Triton; 15% Glycerol; 10 mM βME. Substrate: 2 μM final concentration (from a 2 mM stock solution in DMSO stored at −20° C.). HCV NS3/4A type 1a (1b), 2–3 nM final concentration (from a 5 μM stock solution in 25 mM HEPES, pH7.5, 20% glycerol, 300 mM NaCl, 0.2% Triton-X100, 10 mM βME). For compounds with potencies approaching the assay limit, the assay was made more sensitive by adding 50 μg/ml BSA to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present invention in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel Xl-fit software using the equation, $y=A+((B-A)/(1+((C/x)^D)))$.

All of the compounds tested were found to have IC50s of 0.48 μM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the selectivity of the compounds of the present invention in inhibiting HCV NS3/4A protease as compared to other serine or cysteine proteases.

The specificities of compounds of the present invention were determined against a variety of serine proteases: human sputum elastase (HS), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (CT 2633 application) with some modifications to the serine protease assays.

Each assay included a 2 hr enzyme-inhibitor pre-incubation at RT followed by addition of substrate and hydrolysis to ~30% conversion as measured on a Spectramax Pro microplate reader. Compound concentrations varied from 100 to 0.4 μM depending on their potency.

The final conditions and protocol for the serine protease assays were:

50 mM Tris(hydroxymethyl)aminomethane hydrochloride (Tris-HCl) pH8,
0.5M Sodium Sulfate ($Na_2SO_4$), 50 mM NaCl, 0.1 mM EDTA, 3% DMSO,
0.01% Tween-20 with: 133 μM succ-AAA-pNA and 20 nM HS or 8 nM PPE; 100 μM succ-AAPF-pNA and 250 pM Chymotrypsin.

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel Xl-fit software.

HCV Replicon Cell-based Assay

An HCV replicon whole cell system was established as described by Lohmann V, Korner F, Koch J, Herian U, Theilmann L, Bartenschlager R., Science 285(5424): 110–3 (1999). This system enabled us to evaluate the effects of our HCV Protease compounds on HICV RNA replication. Briefly, using the HCV strain 1B sequence described in the Lohmann paper (Assession number: AJ238799), an HCV cDNA was generated encoding the 5' internal ribosome entry site (IRES), the neomycin resistance gene, the EMCV (encephalomyocarditis virus)-IRES and the HCV nonstructural proteins, NS3–NS5B, and 3' non-translated region (NTR). In vitro transcripts of the cDNA were transfected into the human hepatoma cell line, Huh7. Selection for cells constitutively expressing the HCV replicon was achieved in the presence of the selectable marker, neomycin (G418). Resulting cell lines were characterized for positive and negative strand RNA production and protein production over time.

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin, 1:100 L-glutamine and 5% DMSO in the dilution plate (0.5% DMSO final concentration in the assay). Compound/DMSO mixes were added to the cells and incubated for 4 days at 37° C. After 4 days, plates were rinsed thoroughly with Phosphate-Buffered Saline (PBS) (3 times 150 μl). The cells were lysed with 25 μl of a lysis assay reagent containing the FRET peptide (RET S1, as described for the in vitro enzyme assay). The lysis assay reagent was made from 5× cell Luciferase cell culture lysis reagent(Promega #E153A) diluted to 1× with distilled water, NaCl added to 150 mM final, the FRET peptide diluted to 10 μM final from a 2 mM stock in 100% DMSO. The plate was then placed into the Cytofluor 4000 instrument which had been set to 340 nm excitation/490 emission, automatic mode for 21 cycles and the plate read in a kinetic mode. $EC_{50}$ determinations were carried out as described for the $IC_{50}$ determinations.

As a secondary assay, $EC_{50}$ determinations from the replicon FRET assay were confirmed in a quantitative RNA assay. Cells were lyzed using the Rneasy kit (Qiagen). Purified total RNA was normalized using RiboGreen (Jones L J, Yue S T, Cheung C Y, Singer V L, Anal. Chem., 265(2):368–74 (1998)) and relative quantitation of HCV RNA expression assessed using the Taqman procedure (Kolykhalov A A, Mihalik K, Feinstone S M, Rice C M, Journal of Virology 74, 2046–2051(2000)) and the Platinum Quantitative RT-PCR Thermoscript One-Step kit (Invirrogen cat #11731-015). Briefly, RNA made to a volume of 5 μl (≦1 ng) was added to a 20 μl Ready-Mix containing the following: 1.25×Thermoscript reaction mix (containing Magnesium Sulfate and 2-deoxynucleoside 5'-triphosphates (dNTPs)), 3 mM dNTPs, 200 nM forward primer (SEQ ID NO:1: 5'-gggagagccatagtggtctgc-3'), 600 nM reverse primer (SEQ ID NO:2: 5'-cccaaatctccaggcattga-3'), 100 nM probe (SEQ ID NO:3: 5'-6-FAM-cggaattgccaggacgaccgg-BHQ-1-3')(FAM: Fluorescein-aminohexyl amidite; BHQ: Black Hole Quencher), 1 μM Rox reference dye (Invitrogen cat #12223-012) and Thermoscript Plus Platinum Taq polymerase mixture. All primers were designed with ABI Prism 7700 software and obtained from Biosearch Technologies, Novato, Calif. Samples containing known concentrations of HCV RNA transcript were run as standards. Using the following cycling protocol (50° C., 30 min; 95° C., 5 min; 40 cycles of 95° C., 15 sec, 60° C., 1 min), HCV RNA expression was quantitated as described in the Perkin Elmer manual using the ABI Prism 7700 Sequence Detector.

The luciferase reporter assay was also used to confirm compound potency in the replicon. Utilization of a replicon luciferase reporter assay was first described by Krieger et al (Krieger N, Lohmann V, and Bartenschlager R, J. Virol. 75(10):4614–4624 (2001)). The replicon construct described for our FRET assay was modified by replacing the resistance gene neomycin with the Blasticidin-resistance gene fused to the N-terminus of the humanized form of Renilla luciferase (restriction sites Asc1/Pme1 used for the subcloning). The adaptive mutation at position 1179 (serine to isoleucine) was also introduced (Blight K J, Kolykhalov, A A, Rice, C M, Science 290(5498):1972–1974). The luciferase reporter assay was set up by seeding huh7 cells the night before at a density of $2\times10^6$ cells per T75 flask. Cells were washed the next day with 7.5 ml Opti-MEM. Following the Invitrogen protocol, 40 µl DMRIE-C was vortexed with 5 ml Opti-MEM before adding 5 µg HCV reporter replicon RNA. The mix was added to the washed huh7 cells and left for 4 hours at 37° C. In the mean time, serial compound dilutions and no compound controls were prepared in DMEM containing 10% FCS and 5% DMSO in the dilution plate (0.5% DMSO final concentration in the assay). Compound/DMSO mixes were added to each well of a 24-well plate. After 4 hours, the transfection mix was aspirated, and cells washed with 5 ml of Opti-MEM before trypsinization. Trypsinized cells were resuspended in 10% DMEM and seeded at $2\times10^4$ cells/well in the 24-well plates containing compound or no compound controls. Plates were incubated for 4 days. After 4 days, media was removed and cells washed with PBS. 100 µl 1× Renilla Luciferase Lysis Buffer (Promega) was immediately added to each well and the plates either frozen at −80° C. for later analysis, or assayed after 15 mins of lysis. Lysate (40 µl) from each well was transferred to a 96-well black plate (clear bottom) followed by 200 µl 1× Renilla Luciferase assay substrate. Plates were read immediately on a Packard TopCount NXT using a luminescence program.
The percentage inhibition was calculated using the formula below:

$$\% \text{ control} = \frac{\text{average luciferase signal in experimental wells (+compound)}}{\text{average luciferase signal in DMSO control wells (−compound)}}$$

The values were graphed and analyzed using XLFit to obtain the $EC_{50}$ value.

Biological Examples

Representative compounds of the invention were assessed in the HCV replicon cell assay and/or in several of the outlined specificity assays. For example, Compound 1 was found to have an $IC_{50}$ of 8 nM against the NS3/4A BMS strain in the enzyme assay. Similar potency values were obtained with the published H77C ($IC_{50}$ of 2.2 nM) and J4L6S ($IC_{50}$ of 1.6 nM) strains. The $EC_{50}$ value in the replicon assay was 55 nM.

In the specificity assays, the same compound was found to have the following activity: HS=35 µM; PPE>50 µM; Chymotrypsin>50 µM; Cathepsin B>50 µM (solubility issues at 100 µM). These results indicate this family of compounds are highly specific for the NS3 protease and many of these members inhibit HCV replicon replication.

The compounds of the current invention were tested and found to have activities in the following ranges:

$IC_{50}$ Activity Ranges (NS3/4A BMS Strain): A is 1–10 micromolar (µM); B is 0.1–1 µM; C is <0.1 µM $EC_{50}$ Activity Ranges: A is 1–10 micromolar (µM); B is 0.1–1 µM; C is <0.1 µM Note that by using the Patent compound number shown in the table (below) the structures of compounds can be found herein.

In accordance with the present invention, preferred compounds have a biological activity ($EC_{50}$) of 10 µM or less, more preferably 1 µM or less and most preferably 0.1 µM or less.

| Table 1 of Example 21 Cmpd # | $IC_{50}$ a, b, c | $EC_{50}$ a, b, c |
|---|---|---|
| 1 | C | C |
| 2 | C | B |
| 3 | B | B |
| 4 | C | B |
| 5 | B | A |
| 6 | C | B |
| 7 | C | A |
| 8 | C | B |
| 9 | C | B |
| 10 | C | B |
| 11 | C | A |
| 12 | B | A |
| 13 | C | B |
| 14 | C | B |
| 15 | B | A |
| 16 | C | B |
| 17 | C | B |

Example 22

The following compounds are further examples of compounds that can be made in accordance with the teachings of the present invention.

A

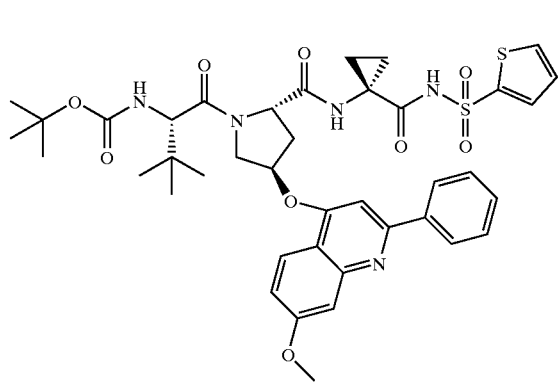

-continued
B
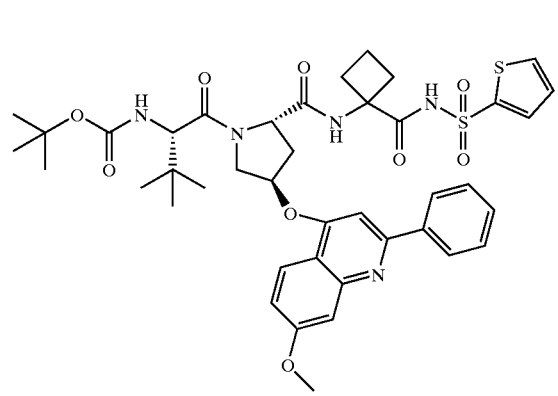
C
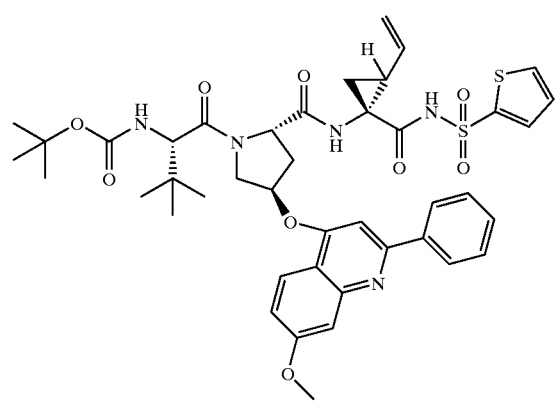
D
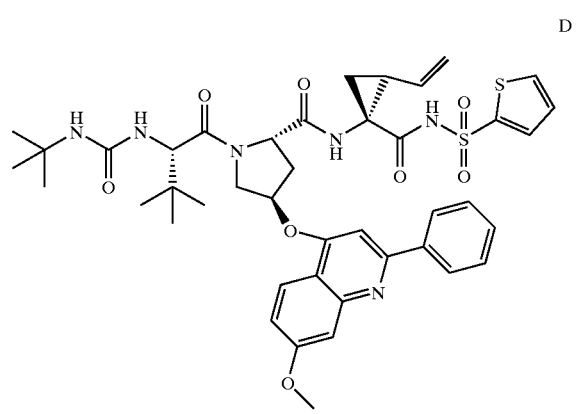
E
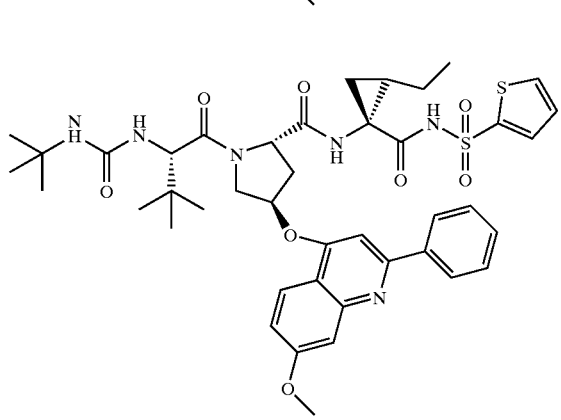
-continued
F
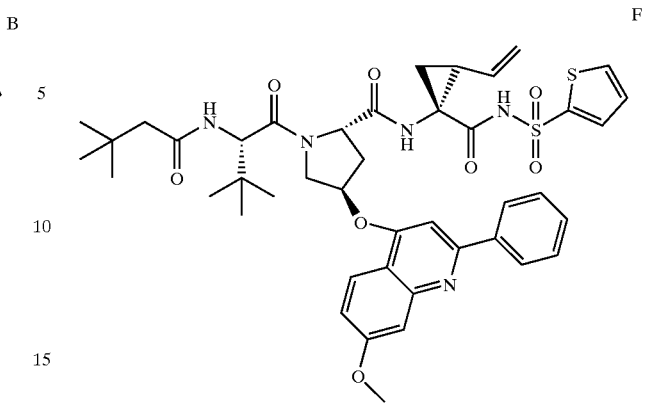
G
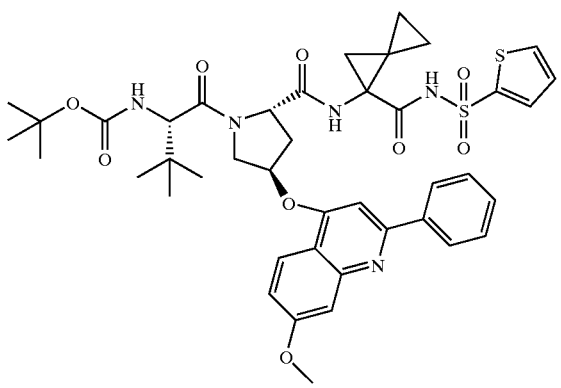
H
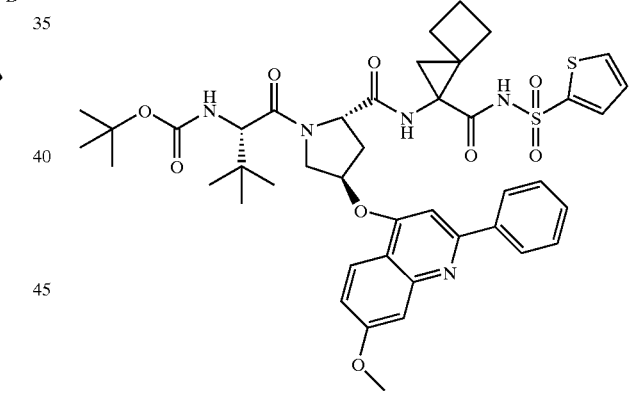
I
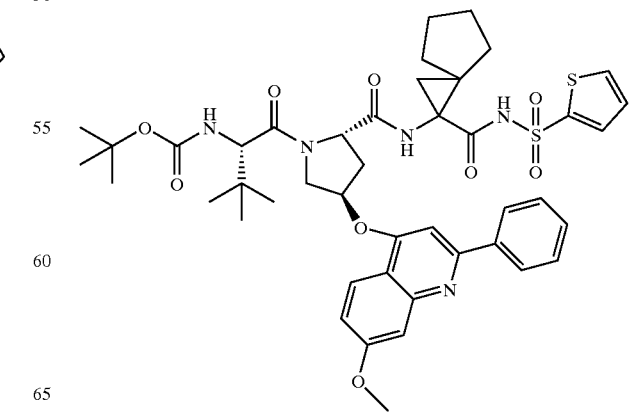

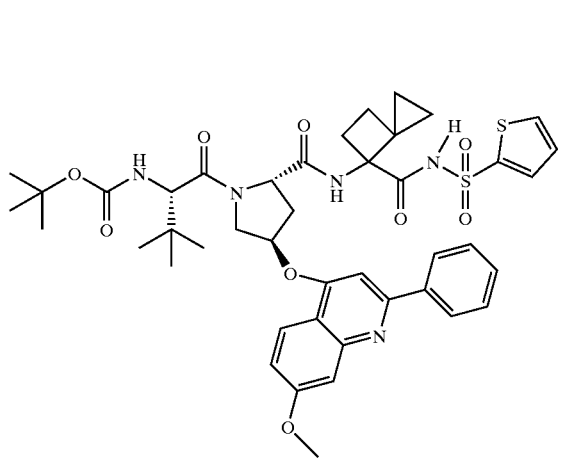

J

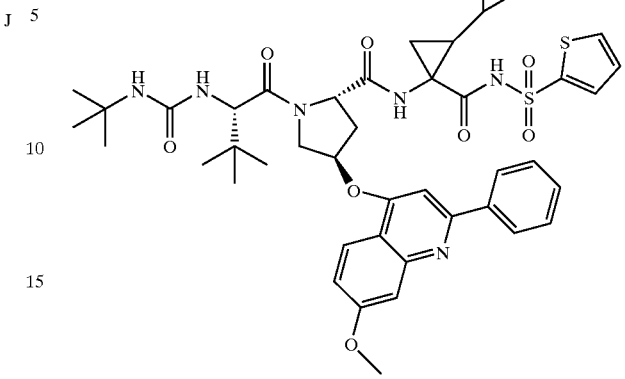

K

Although the invention has been described with respect to specific aspects, those skilled in the art will recognize that other aspects, not specifically described herein, are intended to be included within the scope of the claims that follow.

---

What is claimed is:

1. A compound having the formula

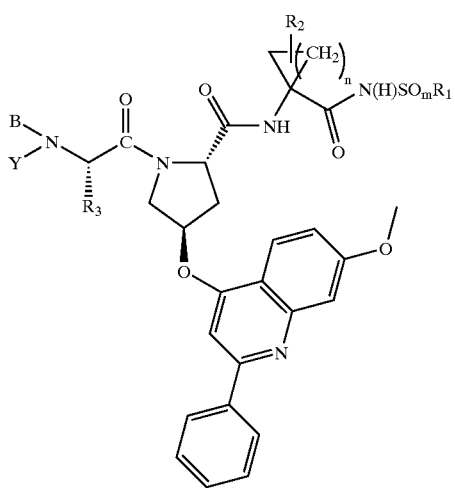

(I)

wherein:
(a) $R_1$ is unsubstituted or substituted Het, said Het substituents being the same or different and being selected from one to three of halo, cyano, trifluoromethyl, nitro, $C_{1-6}$ alkyl, $C_{1-6}$ alkoxy, amido, $C_{1-6}$ alkanoylamino, amino, phenyl or phenylthio, said phenyl or phenyl portion of phenylthio being unsubstituted or substituted by one to three, same or different, substituents selected from halo, cyano, nitro, $C_{1-6}$ alkyl, $C_{1-6}$ alkoxy, amido or phenyl;
(b) m is 1 or 2;
(c) n is 1 or 2;
(d) $R_2$ is $C_{1-6}$ alkyl, $C_{2-6}$ alkenyl or $C_{3-7}$ cycloalkyl, each optionally substituted from one to three times with halogen; or $R_2$ is H; or $R_2$ together with the carbon to which it is attached forms a 3, 4 or 5 membered ring;
(e) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;
(f) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;
(g) B is H, $C_{1-6}$ alkyl, $R_4$—(C=O)—, $R_4O$(C=O)—, $R_4$—N($R_5$)—C(=O)—, $R_4$—N($R_5$)—C(=S)—, $R_4SO_2$—, or $R_4$—N($R_5$)—$SO_2$—;
(h) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo (1.1.1)pentane; or (vi) —C(O)OC$_{1-6}$ alkyl, $C_{2-6}$alkenyl or $C_{2-6}$ alkynyl; and
(i) $R_5$ is H; $C_{1-6}$ alkyl optionally substituted with 1–3 halogens; or $C_{1-6}$ alkoxy provided $R_4$ is $C_{1-10}$ alkyl;
or a pharmaceutically acceptable salt, solvate or prodrug thereof.

2. A compound of claim 1 wherein m is 2.
3. A compound of claim 1 wherein n is 1.
4. A compound of claim 1 wherein $R_1$ is

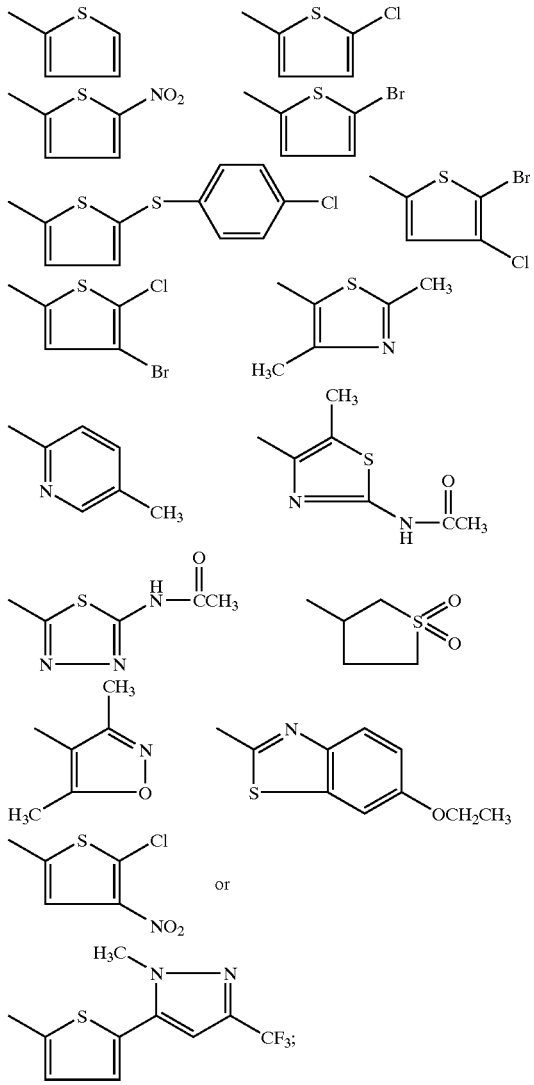

5. The compound of claim 1 wherin $R_2$ is $C_{1-6}$ alkyl, $C_{2-6}$ alkenyl or $C_{3-7}$ cycloalkyl.
6. A compound of claim 5 wherein $R_2$ is ethyl or vinyl.
7. The compound of claim 1 wherein $R_3$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl.
8. The compound of claim 7 wherein $R_3$ is $C_{1-8}$ alkyl optionally substituted with $C_{1-6}$ alkoxy; or $C_{3-7}$ cycloalkyl.
9. A compound of claim 1 wherein $R_3$ is $C_{1-6}$ alkyl.
10. The compound of claim 9 wherein $R_3$ is t-butyl.
11. A compound of claim 1 wherein m is 2, n is 1 and $R_2$ is ethyl.

12. A compound of claim 1 wherein m is 2, n is 1 and $R_2$ is vinyl.

13. The compound of claim 1 wherein Y is H.

14. The compound of claim 1 wherein B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—.

15. The compound of claim 14 wherein B is $R_4$—(C=O)—, $R_4O(C=O)$—, or $R_4$—N($R_5$)—C(=O)—.

16. The compound of claim 15 wherein B is $R_4O$(C=O)— and $R_4$ is $C_{1-6}$ alkyl.

17. The compound of claim 1 wherein $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen.

18. The compound of claim 14 wherein $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl.

19. The compound of claim 18 wherein $R_4$ is t-butyl.

20. The compound of claim 1 wherein $R_5$ is H or $C_{1-6}$ alkyl optionally substituted with 1–3 halogens.

21. The compound of claim 20 wherein $R_5$ is H.

22. A compound of the formula

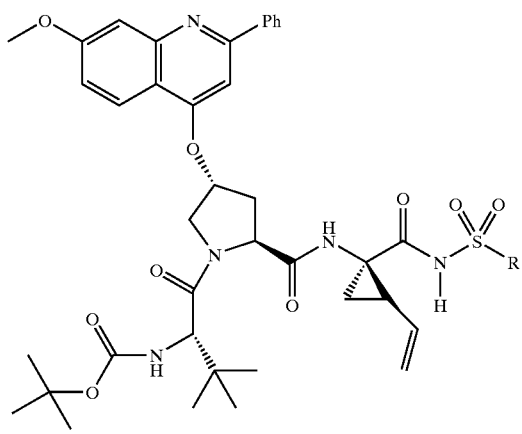

wherein $R_1$ is

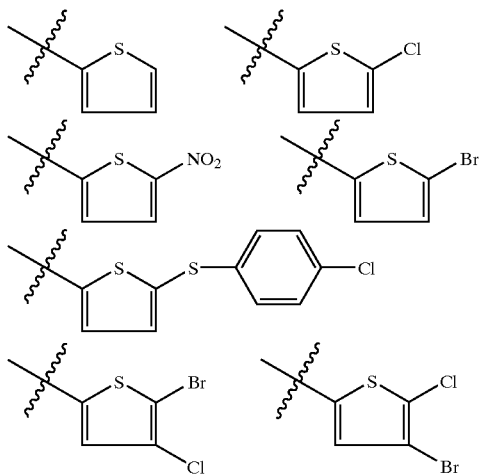

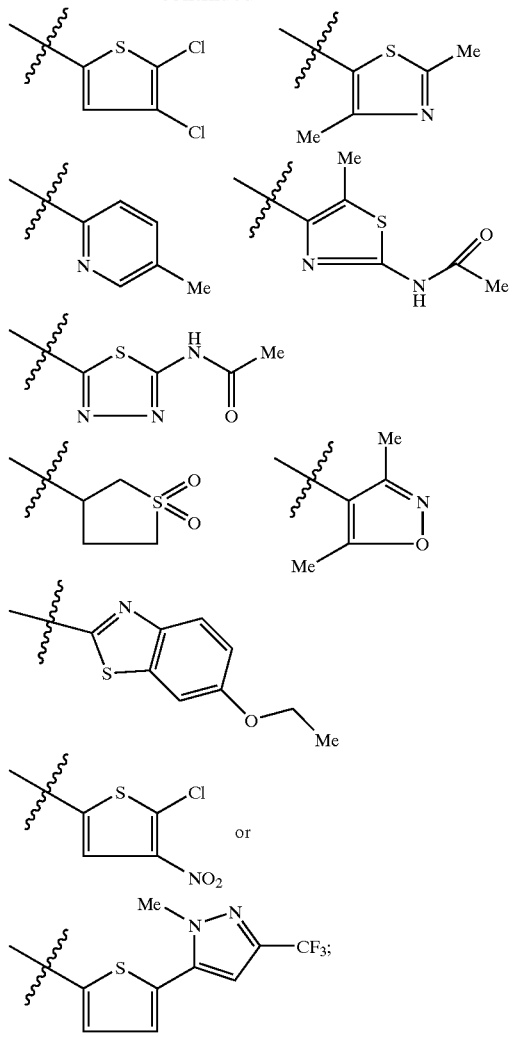

or a pharmaceutically acceptable salt, solvate or prodrug thereof.

23. A method of treating an HCV infection in a patient, comprising administering to the patient a therapeutically effective amount of the compound of claim 1 or a pharmaceutically acceptable salt, solvate or prodrug thereof.

24. A method of inhibiting HCV NS3 protease comprising administering to a patient in need thereof a therapeutically effective amount of the compound of claim 1 or a pharmaceutically acceptable salt, solvate or prodrug thereof.

25. A composition comprising the compound of claim 1 or a pharmaceutically acceptable salt, solvate or prodrug thereof and a pharmaceutically acceptable carrier.

26. The composition of claim 25 further comprising an additional immunomodulatory agent.

27. The composition of claim 26 wherein the additional immunomodulatory agent is selected from the group consisting of α-, β-, and δ-interferons.

28. The composition of claim 25 further comprising an antiviral agent.

29. The composition of claim 28 wherein the antiviral agent is selected from the group consisting of ribavirin and amantadine.

30. The composition of claim 25 further comprising another inhibitor of HCV protease in combination with the compound of claim 1.

31. The composition of claim 25 further comprising an inhibitor of a target in the HCV life cycle other than HCV NS3 protease in with the compound of claim 1.

32. The composition of claim 31 wherein the other target is selected from the group consisting of helicase, polymerase, metalloprotease and mixtures thereof.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: 5' Cloning Primer

<400> SEQUENCE: 1
gggagagcca tagtggtctg c                                      21

<210> SEQ ID NO 2
<211> LENGTH: 20
<212> TYPE: DNA
<213> ORGANISM: Artificial Sequence
<220> FEATURE:
<223> OTHER INFORMATION: 5' Cloning Primer

<400> SEQUENCE: 2
cccaaatctc caggcattga                                        20

<210> SEQ ID NO 3
<211> LENGTH: 21
<212> TYPE: DNA
<213> ORGANISM: Artificial Sequence
<220> FEATURE:
<223> OTHER INFORMATION: 5'-6-FAM Cloning Primer

<400> SEQUENCE: 3
cggaattgcc aggacgaccg g                                      21